US010323289B2

(12) United States Patent
Huot et al.

(10) Patent No.: US 10,323,289 B2
(45) Date of Patent: Jun. 18, 2019

(54) TREATMENTS TO ELIMINATE HIV RESERVOIRS AND REDUCE VIRAL LOAD

(71) Applicant: INSTITUT PASTEUR, Paris (FR)

(72) Inventors: Nicolas Huot, Deuil la Barre (FR); Beatrice Jacquelin, Paris (FR); Michaela Muller-Trutwin, Paris (FR)

(73) Assignee: INSTITUT PASTEUR, Paris (FR)

( * ) Notice: Subject to any disclaimer, the term of this patent is extended or adjusted under 35 U.S.C. 154(b) by 0 days.

(21) Appl. No.: 16/016,912

(22) Filed: Jun. 25, 2018

(65) Prior Publication Data

US 2018/0371556 A1 Dec. 27, 2018

Related U.S. Application Data

(60) Provisional application No. 62/566,907, filed on Oct. 2, 2017, provisional application No. 62/524,996, filed on Jun. 26, 2017.

(51) Int. Cl.
C12Q 1/70 (2006.01)
A61K 38/02 (2006.01)
G01N 33/50 (2006.01)
A61P 31/18 (2006.01)

(52) U.S. Cl.
CPC .............. C12Q 1/703 (2013.01); A61K 38/02 (2013.01); A61P 31/18 (2018.01); G01N 33/502 (2013.01); G01N 33/5091 (2013.01); C12Q 2600/136 (2013.01)

(58) Field of Classification Search
None
See application file for complete search history.

(56) References Cited

U.S. PATENT DOCUMENTS 7,033,582 B2 * 4/2006 Yong ..................... A61K 31/785
424/400
8,628,924 B2 * 1/2014 Kacian ................. C12Q 1/6865
435/6.12

OTHER PUBLICATIONS

Arlettaz et al., "Activating CD94:NKG2C and inhibitory CD94:NKG2A receptors are expressed by distinct subsets of committed CD8+ TCR αβ lymphocytes," Eur. J. Immunol., 34:3456-3464 (2004).
Hansen et al., "Broadly targeted CD8+ T cell responses restricted by major histocompatibility complex E.," Science 351:714-720 (2016).
He et al., "Follicular CXCR5-expressing CD8(+) T cells curtail chronic viral infection." Nature, 537:412-428 (2016).

Jiang et al., "HLA-E-restricted regulatory CD8+ T cells are involved in development and control of human autoimmune type 1 diabetes," J. Clin. Invest., 120:3641-3650 (2010).
Joosten et al., "Characteristics of HLA-E Restricted T-Cell Responses and Their Role in Infectious Diseases," J. Immunol. Res., 11 pages (2016).
Kim et al., "Inhibition of follicular T-helper cells by CD8(+) regulatory T cells is essential for self tolerance," Nature 467:328-U107 (2010).
Kim et al., "CD8+ T regulatory cells express the Ly49 Class I MHC receptor and are defective in autoimmune prone B6-Yaa mice," Proc. Natl. Acad. Sci., 108:2010-2015 (2011).
Leong et al., "CXCR5(+) follicular cytotoxic T cells control viral infection in B cell follicles," Nat. Immunol., 17:1187-1199 (2016).
Miles et al., "Follicular Regulatory CD8 T Cells Impair the Germinal Center Response in SIV and Ex Vivo HIV Infection," PLOS Pathog., 12:e1005924 (2016).
Ramot et al., "Comparative Long-Term Preclinical Safety Evaluation of Two Glatiramoid Compounds (Glatiramer Acetate, Copaxone®, and TV-5010, Protiramer) in Rats and Monkeys," Toxicol. Pathol., 40:40-54 (2011).
Saez-Cirion et al., "Post-treatment HIV-1 controllers with a long-term virological remission after the interruption of early initiated antiretroviral therapy ANRS VISCONTI Study," PLoS Pathog, 9:e1003211 (2013).
Saez-Cirion et al., "Immune responses during spontaneous control of HIV and AIDS: what is the hope for a cure?" Philos Trans R Soc Lond B Biol Sci, 369:20130436. (2014).
Sinha et al., "CD8+ T-Cells as Immune Regulators of Multiple Sclerosis," Front. Immunol., 6:1-12 (2015).
Teitenbaum et al., "Oral Glatiramer Acetate in Experimental Autoimmune Encephalomyelitis: Clinical and Immunological Studies," Ann. N. Y. Acad. Sci., 1029:239-249 (2004).
Tennakoon et al., "Therapeutic Induction of Regulatory, Cytotoxic CD8+ T Cells in Multiple Sclerosis," J. Immunol., 176:7119-7129 (2006).
Yao et al., "Glatiramer acetate ameliorates inflammatory bowel disease in mice through the induction of Qa-1-restricted CD8+ regulatory cells," Eur. J. Immunol., 43:125-136 (2006).

* cited by examiner (Continued)

Primary Examiner — Shanon A. Foley
Assistant Examiner — Myron G Hill
(74) Attorney, Agent, or Firm — Arrigo, Lee, Guttman & Mouta-Bellum LLP

(57) ABSTRACT

The present invention relates to a compound inducing activation of HLA-E-restricted CD8 T cells and/or NK cells in a human subject, and reducing HIV viral load, such as glatiramer acetate and glatiramer acetate related active substances and products, for use in the treatment of HIV infection. Macaques chronically infected by SIV have been treated with glatiramer acetate. One of the animals had already progressed to the stage of AIDS. We injected 18 mg of glatiramer acetate three times per week for only 2 weeks. Surprisingly, a strong impact on viral load was observed in response to the treatment. Viremia decreased by 1 log during glatiramer acetate treatment. Even more surprising was the fact that this decrease persisted after stopping the treatment reaching almost a 2 logs decrease in one animal. This is a major result as compared to cART as stopping cART leads to a rebound of the viral load within days. This decrease was correlated with activation of HLA-E restricted CD8 T cells, but not to other classical CD8+ T cells.

20 Claims, 12 Drawing Sheets

Fig. 12

| TYPE OF MARKERS | | |
|---|---|---|
| Tcells | CD45 | + |
| | CD3 | + |
| | CD20 | - |
| | CD8 | + |
| | CD4 | - |
| | CD95 | + |
| | CD28 | - |
| | CD45RA | + |
| NK | NKG2A | + |
| | NKP30 | - |
| | NKP80 | + |
| homing | CCR7 | + |
| | CD62L | low |
| | CX3CR1 | low |
| | CXCR3 | high |
| | CXCR5 | + |
| others | CD161 | + |
| | IL15-ra | + |

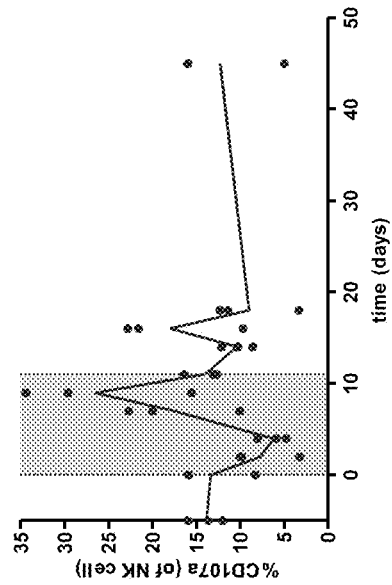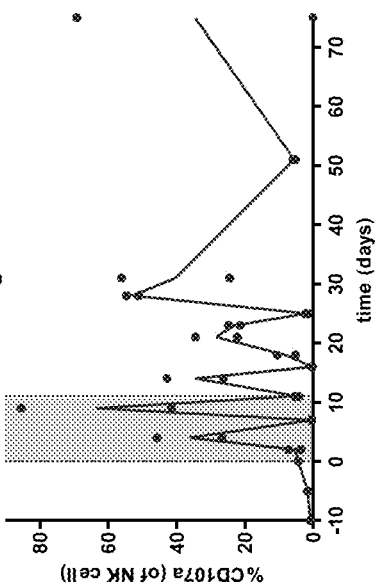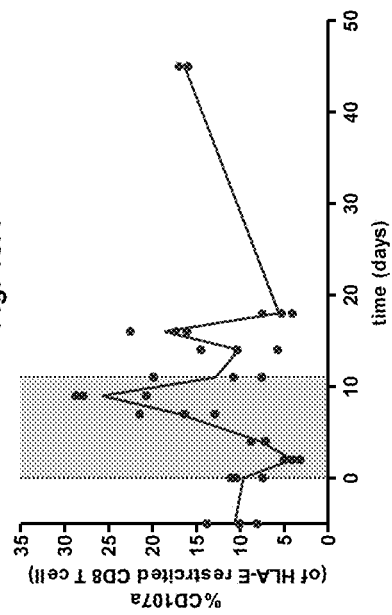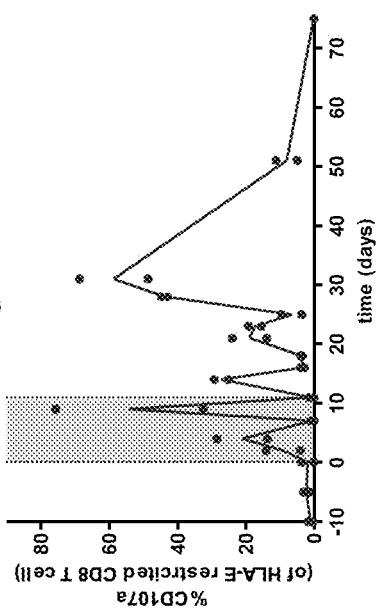

TREATMENTS TO ELIMINATE HIV RESERVOIRS AND REDUCE VIRAL LOAD

FIELD OF THE INVENTION

The present invention relates to a compound such as glatiramer acetate and glatiramer acetate related active substances and products that induce HLA-E-restricted lymphocytes, such as HLA-E-restricted CD8 T cells and/or NK cells, and decrease HIV viral load in a human infected by HIV, for use in the treatment of HIV infection.

BACKGROUND OF THE INVENTION

The implementation of combined antiretroviral therapy (cART) to treat HIV infection has been an incredible success and saved millions of lives. However, HIV remains a major public health issue and represents even today the leading cause of death globally in women with reproductive age (15-49 y) and the 2nd cause of death in adolescents in the world. The number of new infections is not sufficiently decreasing and a vaccine is urgently needed. Moreover, a cure for HIV is still lacking. In people living with HIV, cART treatment does not eliminate the virus from the body. Instead, the virus persists and hides in form of so-called "viral reservoirs". As soon as cART is discontinued, the virus rebounds from the viral reservoirs and rapidly reaches viremia levels as high as before initiation of cART treatment. This persistence of HIV in cellular and anatomical reservoirs requires maintaining the treatment of HIV-infected individuals for their whole lives (Calin et al., 2016; Davey et al., 1999; Lorenzo-Redondo et al., 2016). Lifelong treatment represents a high economical cost. So far, only half of all patients worldwide have access to cART. Long-term efficacy of this treatment is also hampered by issues of drug resistance resulting from poor adherence. The operational and logistical challenges in delivering life-long treatment are indeed daunting. While second and third line drugs exist to combat resistant strains, they are often too expensive in the developing world. Viral load assays for clinical management of the patients and detection of viral resistance are most often not implemented (Chun et al., 2015; Trono et al., 2010). Last but not least, HIV infection is associated in many places with stigma and discrimination. If not diagnosed sufficiently early enough, cART is not capable to restore full immune function. Moreover, the persistent HIV-induced chronic inflammation in most cART-treated individuals induces a higher risk of non-AIDS mortality and co-morbidity.

This is why, HIV researchers have begun to explore a number of novel therapeutic strategiesin view of HIV cure. Many approaches (TLR-7, latency reversal agents, CMV vaccination, bNabs, anti-a4b7) are currently tested. The path toward a therapy for HIV cure is however very long. Multiple obstacles must be overcome to reach a persistent control or even elimination of HIV. In particular, HIV has a remarkable capacity to mutate and escape adaptive immune responses. Furthermore, HIV infection induces immunological dysfunction and consequently, the host fails to control viral replication. Moreover, the genetic material of the virus is integrated into the cellular genome, which allows the virus to become invisible and evade the host's immune responses. In this way, HIV can persist in the body for the whole life span of the host.

The case of Timothy Brown has raised hope that a HIV cure might nonetheless be feasible. Timothy Brown is an HIV-infected patient with cancer who received a double stem cell transplant from a donor whose $CD4^+$ T cells were resistant to HIV infection thanks to a CCR5Δ32 mutation (Allers et al, 2011; Hutter et al, 2009). Since the transplantation 10 years ago, Timothy Brown is living without detectable virus and he represents the closest and only example to an HIV cure to date. However, achieving HIV eradication in a large population of patients with scalable and safe therapies seems farfetched at present.

More recently, cases of HIV remission have been described (Saez-Cirion et al., 2014). In analogy to cancer, HIV remission means that the while the virus is not eradicated, the patient is healthy, capable to control by its own the virus and does not need any drugs any more. HIV remission is also called functional cure. These few HIV-infected individuals in remission had started cART treatment early, already during the acute phase of infection, which is rather rare. Fourteen of these patients spontaneously controlled viral replication after cART interruption. Those patients had a small viral reservoir at the time of therapy interruption (Saez-Cirion et al., 2013). However, the patients did not show any particular strong classical B or T cell responses against HIV and thus the mechanisms of viral control leading to remission are unclear.

HIV originates from the Simian Immunodeficiency Virus (SIV) whose reservoir resides in African non human primates. Remarkably, the natural hosts of SIV, such as African green monkey (AGM), are resistant to AIDS (Chahroudi et al., 2012). This contrast with Asian monkeys (macaques) that are not infected in the wild and develop AIDS when infected with SIV (Garcia-Tellez et al., 2016; Ploquin et al., 2016). Similarly to HIV-infected individuals, SIVmac in macaques replicates to high levels in lymphoid tissues, in particular secondary lymphoid organs and intestinal mucosa. Important target cells for HIV and SIVmac viruses in these tissues are the central memory CD4 T cells ($T_{CM}$) as well as transitional memory CD4 T cells ($T_{TM}$) (Chomont et al., 2009; Descours et al., 2012). More recently though it has been shown that follicular helper CD4 T cells ($T_{FH}$) that are localized in follicles of lymphoid tissues constitute the major reservoir of HIV and SIV (Banga, 2016; Buranapraditkun et al., 2017; Fukazawa et al., 2015; Miles and Connick, 2016a; Miles and Connick, 2016b; Moukambi et al., 2017).

SIV infection in AGM has been studied in order to identify factors responsible for protection against AIDS (Garcia-Tellez et al., 2016). Strikingly lymph nodes and spleen display extremely low levels of SIV in AGM (Brenchley et al., 2012; Gueye et al., 2004). SIVagm infection of $T_{CM}$ is rare and $T_{FH}$ are generally not infected at all in natural hosts (Brenchley et al., 2012; Cartwright et al., 2014; Paiardini et al., 2011; Ploquin et al 2016).

$T_{FH}$ cells are known to express high levels of HLA-E, the least polymorphic of all the MHC class Ib molecules. Under physiological conditions, HLA-E specifically binds the signal peptide derived from classical HLA class-Ia molecules, such as HLA-B. The expression of HLA-E at the cell surface is enhanced through the binding of such intracellular peptides. HLA-E interacts with CD94/NKG2A receptors expressed on the surface of natural killer (NK) cells and a small subset of CD8 T cells (Arlettaz et al., 2004). In addition, these CD8 T cells may specifically recognize foreign peptides presented by HLA-E and become activated through their T cell receptor (TCR), resulting in T cell activation, expansion, and memory formation in the adaptive immune system (Joosten et al., 2016). Presentation of the signal peptide by HLA-E protects the cell from being killed (Lee et al., 1998). In some situations, such as cellular stress and infections, HLA-E can bind other self-peptides such as the HSP60-derived peptides and also pathogen-derived sequences, rendering these cells more susceptible to attack by the innate and adaptive immune responses (Michaëlsson et al., 2002; Anraku et al., 2012).

HLA-E restricted CD8 T cells have been more studied in mice, where the molecule Qa-1 is the equivalent of HLA-E. The cells express effector cell markers, lymph node homing receptors and NK cell markers such as NKG2A, CD45RA, CCR7 and low levels of CXCR5 and ICOSL (He et al., 2016; Joosten et al., 2016; Kim et al., 2011; Lu and Cantor, 2008; Miles et al., 2016b). They also express CD122 and are IL-15-dependent. They play an important role in maintenance of self-tolerance and prevention of autoimmune disease (Kim et al., 2010; Long et al., 2017). In humans, a specific defect in the recognition of HLA-E/HSP60-peptides by HLA-E restricted CD8 T cells was associated with failure of self/non-self discrimination in type 1 diabetes, confirming that they play an important role in keeping self-reactive T cells in check (Jiang et al., 2010). In this regard, patients with type 1 diabetes harbor increased HSP60 levels (Devaraj et al., 2009; Shamaei-Tousi et al., 2006).

During lymphocytic choriomeningitis virus infection in mice, it has been shown that HLA-E restricted CD8 T cells can clear the persisting virus from $T_{FH}$ and B cells (He et al., 2016; Leong et al., 2016).

HIV-infection induces an enhanced expression of HLA-E resulting in reduced susceptibility to NK cell cytotoxicity (Nattermann et al., 2005). In some cases, the capacity to escape target cell lysis by NK cells, might outweight the potential risk of increased susceptibility to HLA-E-restricted CD8 T cells (Gong et al., 2012; Hansen et al., 2016; Joosten et al., 2016). HLA-E restricted CD8 T cells have been described in the tonsils of HIV-infected patients and in the lymph nodes and spleen of SIV-infected macaques and called "follicular regulatory CD8 T cells" (CD8 $T_{FR}$) (Miles et al., 2016b). Their percentages increase with infection and lead to a potent impairment of $T_{FH}$ and germinal center B cell responses. HLA-E-restricted CD8 T cells are actually poorly primed during SIV/HIV infection. It is however not clear if these cells are the same than the HLA-E restricted CD8 T cells described in other studies or a new not yet described cell subset. We have (i) further characterized HLA-restricted T and NK cells (ii) studied if they can be experimentally induced by a drug in a non human primate model of HIV and (iii) analyzed the impact of this drug on viral load control during and after treatment cessation.

BRIEF SUMMARY OF THE INVENTION

The invention encompasses compositions, methods, and uses of compounds, such as glatiramer acetate, that increase activation of HLA-E-restricted lymphocytes such as HLA-E restricted CD8 T cells and/or NK cells in an HIV-infected human.

The invention encompasses a compound inducing activation of HLA-E-restricted CD8 T cells and/or NK cells in a human subject, for use in the treatment of HIV infection. In one embodiment, the HLA-E-restricted CD8 T cells and/or NK cells are expressing NKG2A/C. In one embodiment, the HLA-E-restricted CD8 T cells and/or NK cells are expressing CD107a.

In one embodiment, the compound is Glatiramer acetate (GA) for use in treating HIV-infected human subjects. In one embodiment, the HIV-infected patient undergoing cART. In one embodiment, the HIV-infected patient which never initiated cART.

In one embodiment, the GA is L-glutamic acid polymer with L-alanine, L-lysine and L-tyrosine, acetate (salt) of formula: (Glu,Ala,Lys,Tyr)x.X.CH3COOH. In one embodiment, the compound is COPAXONE®, GLATOPA®, or BRABIO®, or generic forms or products thereof. In one embodiment, the GA is in the form of a product for subcutaneous injection.

In one embodiment, the HIV-infected patient is acutely infected with HIV. In one embodiment, the HIV-infected patient is chronically infected with HIV. In one embodiment, the HIV-infected patient has previously undergone cART, and either ceases or continues cART.

In one embodiment, the GA is administered at least twice/day, twice/week, once/day, once/week, three times/week, or once/every 2 days. In one embodiment, at least 10, 15, 20, 25, 30, 35, 40, 45, 50, 55, 60, 65, 70, 75, 80, 100, 120, or 160 mg of GA is administered.

In one embodiment, the compound is administered in conjunction with an HIV inhibitor. In one embodiment, the compound is administered in conjunction with at least 2 or 3 HIV inhibitors. In one embodiment, the compound is administered in conjunction with cART. In one embodiment, the cART comprises Combivir, Kaletra, Trizivir, Epzicom, Kivexa, Truvada, Atripla, Complera, Eviplera, Stribild, Triumeq, Evotaz, Prezcobix, Dutrebis, Genvoya, or Descovy. In one embodiment, the cART comprises at least 2 or 3 of any of the following compounds: lamivudine; zidovudine; lopinavir; ritonavir; abacavir; tenofovir disoproxil fumarate; emtricitabine; efavirenz; rilpivirine; elvitegravir; cobicistat; dolutegravir; atazanavir; cobicistat; darunavir; and raltegravir. In one embodiment, the HIV inhibitor comprises a Rev inhibitor.

In one embodiment, the HIV-infected patient has never been diagnosed with Multiple sclerosis. In one embodiment, the HIV-infected patient has never been diagnosed with HIV encephalopathy.

In one embodiment, the compound is a Glatiramer acetate related drug substance or product characterized by the process comprising the steps of: administering a suitable amount of the Glatiramer acetate related drug substance, or drug product in a non human mammal and determining the activation level of HLA-E-restricted CD8 T cells and/or NK cells in said mammal compared to a baseline level, wherein an increase in activation of HLA-E-restricted CD8 T cells and/or NK cells, such as an increase of the number of cells HLA-E-restricted CD8 T cells and/or NK cells expressing NKG2A/C and/or CD107a in said mammal characterizes said GA related substance or product as a product for treating HIV infection in humans. In one embodiment, the invention encompasses such a process.

In one embodiment, the invention encompasses a method for measuring the effect of a compound that increases HLA-E-restricted cell activity, in particular that increases HLA-E restricted CD8 T cells and/or NK cells, on an HIV-infected human comprising administering at least one dose of a compound that increases HLA-E-restricted CD8 T cells to the human; and measuring the level of HIV infection in the HIV-infected human.

In one embodiment, the invention encompasses a method for measuring the effect of glatiramer acetate on an HIV-infected human comprising administering at least one dose of glatiramer acetate to the HIV-infected human; and measuring the level of HIV infection in the HIV-infected human.

In various embodiments, measuring the level of HIV infection in the HIV-infected human comprises measuring the level of plasma HIV RNA in the HIV-infected human. In various embodiments, measuring the level of plasma HIV RNA in the HIV-infected human is performed by a reverse transcription and amplification reaction. In various embodiments, the level of HIV infection in the human is measured at least 2, 3, 4, 5, 6, 7, 8, 9, or 10 times. In various embodiments, the level of HIV infection in the human is compared to a measurement taken before treatment with the compound.

In various embodiments, the HIV-infected human has never been diagnosed with multiple sclerosis. In various embodiments, the HIV-infected human has never been diagnosed with HIV-1 associated cognitive impairment. In various embodiments, the HIV-1 infected patient is acutely infected with HIV. In various embodiments, the HIV-1 infected patient is chronically infected with HIV. In various embodiments, the HIV-1 infected patient is undergoing cART. In various embodiments, the HIV-1 infected patient has never initiated cART. In various embodiments, the HIV-1 infected patient has previously undergone cART, and either ceases or continues cART.

In various embodiments, at least 2, 3, 4, 5, 6, 7, 8, 9, 10-20, 20-50, or 50-100 administrations are given. In various embodiments, the administration is given at least twice/day, twice/week, once/day, once/week, three times/week, or once/every 2 days. In various embodiments, at least 10, 15, 20, 25, 30, 35, 40, 45, 50, 55, 60, 65, 70, 75, 80, 100, 120, or 160 mg of the compound is administered. In various embodiments, at least 20 mg/day of the compound is administered. In various embodiments, at least 40 mg of the compound is administered at least three times/week.

The invention encompasses a method for treating an HIV infection in a human comprising administering a pharmaceutical composition comprising an effective amount of glatiramer acetate to an HIV-infected human; wherein the administration of glatiramer acetate reduces the level of plasma HIV RNA in the HIV-infected human. The invention further encompasses a pharmaceutical composition for use in treating an HIV-infected human comprising an effective amount of glatiramer acetate. The invention further encompasses the use of a pharmaceutical composition comprising glatiramer acetate in the treatment of an HIV infection in a human patient.

In various embodiments, the administration of glatiramer acetate reduces the level of plasma HIV RNA in the HIV-infected patient at least 10-fold. In various embodiments, the administration of glatiramer acetate reduces the level of plasma HIV RNA in the HIV-infected patient at least 100-fold. In various embodiments, the reduction is assessed at 4-52 weeks after administration of glatiramer acetate. In various embodiments, the reduction is assessed at multiple times after administration of glatiramer acetate.

In various embodiments, the pharmaceutical composition comprises at least 10, 15, 20, 25, 30, 35, 40, 45, 50, 55, 60, 65, 70, 75, 80, 100, 120, or 160 mg of glatiramer acetate.

In various embodiments, the HIV-infected human has never been diagnosed with multiple sclerosis. In various embodiments, the HIV-infected human has never been diagnosed with HIV-1 associated cognitive impairment. In various embodiments, the HIV-1 infected patient is acutely infected with HIV. In various embodiments, the HIV infected patient is chronically infected with HIV. In various embodiments, the HIV-infected patient is undergoing cART. In various embodiments, the HIV-infected patient has never initiated cART. In various embodiments, the HIV infected patient has previously undergone cART, and either ceases or continues cART. HIV infection is meant in the context herein to refer to HIV-1 or HIV-2 infection.

In various embodiments, at least 2, 3, 4, 5, 6, 7, 8, 9, 10-20, 20-50, or 50-100 administrations are given. In various embodiments, the administration is given at least twice/day, twice/week, once/day, once/week, three times/week, or once/every 2 days. In various embodiments, at least 10, 15, 20, 25, 30, 35, 40, 45, 50, 55, 60, 65, 70, 75, 80, 100, 120, or 160 mg/day is administered. In various embodiments, at least 20 mg/day is administered. In various embodiments, at least 40 mg is administered at least three times/week.

The invention further encompasses a pharmaceutical composition for use in treating an HIV-infected human comprising an effective amount of glatiramer acetate and an HIV inhibitor. The invention also encompasses a kit of parts for simultaneous, separate, sequential administration to an HIV-infected patient comprising an effective amount of glatiramer acetate and an HIV inhibitor.

In various embodiments, the pharmaceutical composition or the kit of parts comprises at least 2 or 3 HIV inhibitors. In various embodiments, the pharmaceutical composition or the kit of parts comprises cART. In various embodiments, the pharmaceutical composition or the kit of parts comprises a Rev inhibitor.

In various embodiments, the cART comprises Combivir, Kaletra, Trizivir, Epzicom, Kivexa, Truvada, Atripla, Complera, Eviplera, Stribild, Triumeq, Evotaz, Prezcobix, Dutrebis, Genvoya, or Descovy.

In various embodiments, the cART comprises at least 2 or 3 of any of the following compounds: lamivudine; zidovudine; lopinavir; ritonavir; abacavir; tenofovir disoproxil fumarate; emtricitabine; efavirenz; rilpivirine; elvitegravir; cobicistat; dolutegravir; atazanavir; cobicistat; darunavir; and raltegravir.

In various embodiments, the HIV inhibitor comprises 8-chloro-N-(4-(trifluoromethoxy)phenyl)quinolin-2-amine (ABX464) and 8-chloro-N-glucuronide-N-(4-(trifluoromethoxy)phenyl)quinolin-2-amine) (ABX464-N-glucuronide).

In still another embodiment, the invention relates to a package for treating HIV infected individuals, said package comprising a first product comprising Glatiramer acetate, and a second product comprising at least one, two or three HIV inhibitors as defined above.

In still another embodiment, the invention relates to a package for treating HIV infected individuals, said package comprising a first product comprising Glatiramer acetate, and a second product comprising an HIV rev inhibitor, such as 8-chloro-N-(4-(trifluoromethoxy)phenyl)quinolin-2-amine (ABX464) and 8-chloro-N-glucuronide-N-(4-(trifluoromethoxy)phenyl)quinolin-2-amine) (ABX464-N-glucuronide).

In still another embodiment, the invention relates to a package for treating HIV infected individuals, wherein said package comprises a first product comprising Glatiramer acetate, a second product comprising an HIV rev inhibitor, such as 8-chloro-N-(4-(trifluoromethoxy)phenyl)quinolin-2-amine (ABX464) and 8-chloro-N-glucuronide-N-(4-(trifluoromethoxy)phenyl)quinolin-2-amine) (ABX464-N-glucuronide) and a third product comprising at least 2 or 3 of any of the following compounds: lamivudine; zidovudine; lopinavir; ritonavir; abacavir; tenofovir disoproxil fumarate; emtricitabine; efavirenz; rilpivirine; elvitegravir; cobicistat; dolutegravir; atazanavir; cobicistat; darunavir; and raltegravir.

BRIEF DESCRIPTION OF THE DRAWINGS

FIG. 1A Example of flow cytometry phenotyping of HLA-E restricted CD8 T cells in one healthy AGM and macaque. The flow cytometry phenotyping of AGM and MAC immune cells has been performed as previously described (Jacquelin et al, 2009; Huot et al, 2017). HLA-E restricted CD8 T cells were defined as CD45+CD20−CD3+ CD8+NKG2A/C+ cells. HLA-E in human is equivalent to MHC-E in non human primates. FIG. 1B/Levels of circulating MHC-E restricted CD8 T cells in healthy AGM and macaques. FIG. 1C/Levels of circulating MHC-E restricted CD8 T cells in chronically SIV infected AGM and macaques. Data are presented as medians and interquartile ranges. ****Mann-Whitney test, p<0.0001.

(FIG. 9A). The grey area indicates the period of GA treatment. Correlation between the plasma viral load and the classical CD8 T cells (FIG. 9B) and with the HLA-E restricted CD8 T cells (FIG. 9C) were evaluated. The Spearman coefficients (r) and p-values are indicated.

FIG. 10A) Flow cytometry dot plots. $CD32a^{high}HLA$-$E^+$ $CD4^+$ T cells from AGM and macaques are shown in blue. FIG. 10B) $CD32a^{high}HLA$-$E^+$ $CD4^+$ T cells evaluated in the spleen of 10 AGM, 10 macques and 2 macaques treated with GA. Tx=GA treatment. MAC=macaque.

FIG. 11A: Percentage of MHC-E restricted CD8 T cells (black) as compared to the percentage of memory CD4 T cells (grey) at euthanasia in the tissues of the chronically SIV infected macaque treated with GA and not yet in "AIDS stage". FIG. 11B: Comparison of the percentage of MHC-E restricted CD8 T cells of this same macaque with those of chronically SIV infected and not treated macaques and chronically SIV infected AGM in the gut.

FIG. 12: Phenotype of MHC-E restricted CD8 T cells in AGM. Several proteins that are expressed on NKG2A/C CD8 T cells in AGM and macaques are shown here.

FIG. 13A-D. Follow-up of the cytotoxicity marker CD107a on HLA-E restricted CD8 T cells and on NK cells in 3 healthy cynomolgus macaques (FIG. 13A and FIG. 13B) and 2 chronically SIV-infected cynomolgus macaques (FIG. 13C and FIG. 13D) treated with GA between day 0 and 11. The NK cells have been defined as previously reported (Jacquelin et al, 2014; Huot et al, 2017). The bold lines represent the median and the grey area indicates the period of GA treatment.

DETAILED DESCRIPTION OF THE INVENTION

Figure 1A:
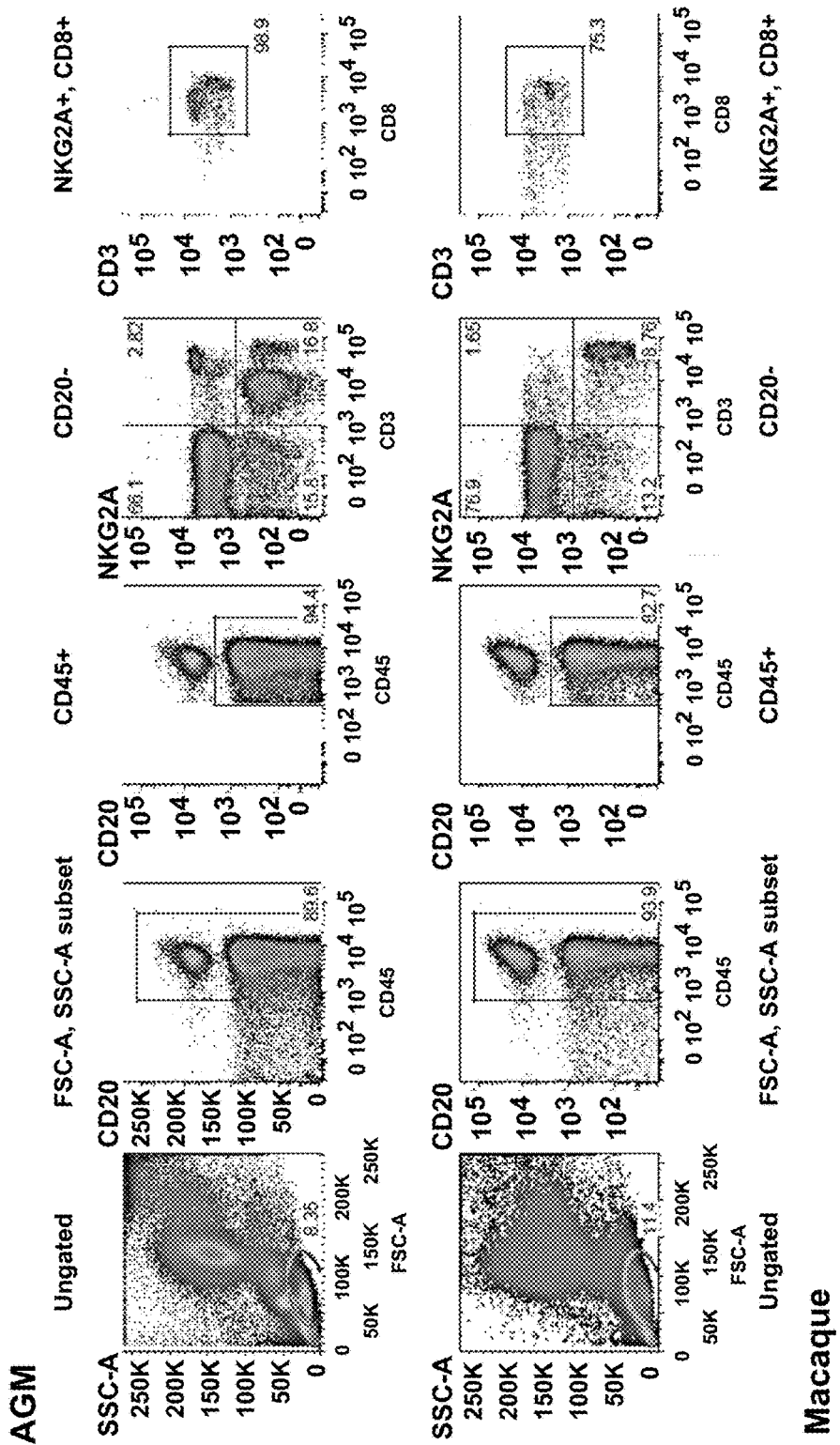
FIG. 1A-C.

The rare cases of patients presenting a durable control of viral replication after treatment interruption suggests that ways exist to induce such a state of HIV remission. Within the last few years, it has become clear that HLA-E restricted CD8 T cells probably play an important role in regulation of viral infections (Joosten et al., 2016). These cells are however only poorly characterized. We raised the hypothesis that if these anti-viral HLA-E restricted lymphocytes such as CD8 T cells and/or NK cells could be induced in humans, this may enable targeting the $T_{FH}$ and eventually other memory CD4 T cell subsets that harbor persistent HIV-1 as a reservoir.

HLA-E restricted CD8 T cells can be induced therapeutically by Glatiramer Acetate treatment (GA; Copaxone) (Sinha et al., 2014, 2015; Tennakoon et al., 2006). GA is a synthetic copolymer composed of four amino acids found in myelin basic protein. It is an FDA-approved drug that has been on the market for more than 20 years and used for its immunomodulatory properties in the long-term management of multiple sclerosis (Sinha et al., 2015). This drug has a remarkable safety profile. It is well tolerated in macaques even at doses that are sixteen-fold higher than the equivalent human dose for 52 weeks (Ramot et al., 2011a). Interestingly, GA has also been shown to be efficient in a mouse model of inflammatory bowel diseases. In this case, the GA-induced HLA-E restricted CD8 T cells target the pathogenic CD4 T cells which were inducing colitis progression (Yao et al., 2013).

We show here that a two weeks treatment with GA in the macaque model of HIV infection allowed up to a 2 logs decrease of viremia in less than 2 months. While the results with the GA are based on a pilot study with only 2 animals, this is the first time that a treatment given on a short time period during chronic HIV/SIV infection in humans or monkeys, in the absence of anti-retroviral therapy, induces such a decrease of viral load that continues when the therapy is interrupted.

Our results revealed also for the first time that HLA-E restricted CD8 T cells are expanded during non-pathogenic SIV infection. Such cells are inducible by GA and thus might be key players of the viral control observed here. Little is known about HLA-E-restricted CD8 T cells and their relevance in vivo. We have characterized them phenotypically and molecularly. We show that they express gut markers, suggesting that they might reduce viral reservoirs in the gut as well. By preventing the virus to replicate in the gut, these cells would participate to the maintenance of the intestinal barrier and prevent the microbial product linkage. This is also a major result, as this mechanism would allow dampening chronic inflammation normally induced by HIV/SIV and reduced but not eliminated by cART.

While we cannot exclude that other or additional mechanisms than the expansion of the CD8 T and NK cell subpopulations is responsible for the viral control, the data indicate that GA induces a rapid and unforeseen durable decrease in viremia in the animal model of HIV.

HIV-infected individuals who efficiently control viral replication because they are under cART regimen still display persistent levels of virus in tissues. Most HIV-infected individuals, who interrupt antiretroviral treatment, display a strong viral rebound within days or weeks. Interestingly, a few HIV-infected individuals who started cART treatment early, spontaneously controlled viral replication after treatment interruption. Those are the patients with a small viral reservoir. Therapies that would allow achieving such low viral reservoirs, which normally are not reached by cART alone, would be of enormous importance.

Our results indicate that GA can reduce the viral reservoirs in an animal model of HIV. Given the fact that this drug has been used in MS patients for >20 years, it has already been proven to be safe in humans and is an interesting candidate to test for a potential therapeutic approach for HIV remission. We propose that treating the patients with GA in combination with the antiretroviral treatment should decrease the viral reservoirs even further than with cART alone and therefore increase the probability for HIV remission and even HIV cure. Such a therapy would be of clinical benefit for millions of people infected by HIV and have a strong societal and economical impact worldwide.

The magnitude of the viral reservoir is strongly associated with the residual levels of inflammation that persists during cART (Massanella et al., 2016). Reducing the viral reservoir would allow to reduce the level of chronic inflammation and thus reduce the risk of non-AIDS mortality and morbidity in the cART-treated patients.

If the treatment is started early on, the induction profile of the HLA-E restricted CD8 T cells would look like the profile obtained in the natural host. This might lead to an early control of the viral reservoir and reduce even more the inflammation. Thus GA administration during the early phase of infection, in combination with cART, might be even more effectively purging HIV infection, allowing to achieve even better HIV remission.

GA treatment in MS patients is generally performed for many years. The information collected from prospective long-term follow-up of patients treated with GA for >10 years provide clear evidence for the long-term efficacy and adequate safety of this immunomodulatory treatment (Brochet et al, 2008). Here we treated the macaques for only a very short period (2 weeks). Because of the beneficial impact on control of virus and its associated inflammation, treatment for longer periods can be significantly stronger and increase the success rate of achieving HIV remission.

The invention relates to various compositions, methods, and uses of a compound that increases HLA-E restricted lymphocytes such as HLA-E-restricted CD8 T cells and/or NK cells, preferably glatiramer acetate, for use in HIV-infected patients.

As used herein, the terms "increase", "induce", "activate", induce activation", increase activation" are used interchangeably to designate the increase of cell number and/or cell activity, with respect to HLA-E restricted lymphocytes such as HLA-E-restricted CD8 T cells and/or NK cells. The increase of cell activity may include the increase of effector cells, as shown in the examples of the present application. The increase of HLA-E restricted lymphocytes is assayed by standard assays such as those disclosed in the present application. The increase may be assayed in various samples comprising lymphocytes such as blood, lymph nodes, or others.

Screening Methods

The invention encompasses various screening methods for determining the effect of a compound that increases HLA-E-restricted CD8 T cells and/or NK cells in a Human Immunodeficiency Virus-infected human.

In one embodiment, the method comprises administering at least one dose of the compound to the human; and measuring the level of HIV infection in the human. In one embodiment, the method comprises administering at least one dose of the compound to the human; and measuring the level of plasma HIV RNA in the human. In one embodiment, the method comprises administering at least one dose of the compound to the human; and measuring the level of HIV-infected reservoir cells in the human.

In one embodiment, the method comprises administering at least one dose of glatiramer acetate to the human; and measuring the level of HIV infection in the human. In one embodiment, the method comprises administering at least one dose of glatiramer acetate to the human; and measuring the level of plasma HIV RNA in the human. In one embodiment, the method comprises administering at least one dose of glatiramer acetate to the human; and measuring the level of HIV-infected reservoir cells in the human.

The invention encompasses a method for measuring HIV infection in an HIV-infected human comprising providing a biological sample from a HIV infected patient treated with a compound that increases HLA-E-restricted CD8 T cells and/or NK cells, expressing NKG2A/C and/or CD107a, in an HIV-infected human comprising:

administering at least one dose of a compound that increases HLA-E-restricted CD8 T cells and/or NK cells expressing NKG2A/C and/or CD107a, to the human; and measuring the level of HIV infection in the HIV-infected human.

The invention also relates to a method for measuring HIV infection in an HIV-infected human comprising:

a) providing a biological sample from a HIV infected patient treated with a compound that increases HLA-E-restricted CD8 T cells and/or NK cells expressing NKG2A/C and/or CD107a, b) measuring the level of HIV infection in the HIV-infected patient.

The invention further encompasses a method for measuring HIV infection in an HIV-infected human comprising providing a biological sample from a HIV infected patient treated with glatiramer acetate or GA related active substance or product, such as Copaxone®, GLATOPA®, or BRABIO®, or generic forms or products thereof, and measuring the level of HIV infection in the HIV-infected patient.

Thus, the invention encompasses method for detecting the presence or absence of HIV-specific nucleic acid, in particular HIV-1-specific nucleic acid, comprising: preparing RNA from a biological sample from an HIV-infected patient treated with at least one dose of glatiramer acetate and detecting the presence or absence of HIV-specific nucleic acid, in particular HIV-1-specific nucleic acid, in the biological sample.

The measurement can provide for a comparison to another infected individual that does not receive the compound or to a prior measurement from that same infected individual, preferably before treatment with the compound. Preferably, the measurement of the level of HIV infection in the human is performed at least twice. In some embodiments, the measurement is taken 3, 4, 5, 6, 7, 8, 9, or 10 times. In this way, the measurements can provide for a comparison over time within that infected individual, most preferably with a measurement taken before treatment with the compound The level of HIV infection can be assessed by different techniques known to the skilled artisan. For example, the level of HIV infection in the human can be determined by measuring the level of plasma HIV RNA in the human. The level of HIV infection can be measured by determining the level of viral RNA, viral DNA, viral protein, or infectious virus in the human by well-known techniques in the art. The measurement can be made using a cell, RNA, DNA, or protein, or other biological sample, such as a blood, serum, plasma, saliva sample.

In one embodiment, the invention encompasses a method comprising providing a biological sample from a HIV-infected patient treated (preferably within 1, 2, 3, 6, or 12 months prior to taking the sample from the patient) with a compound that increases HLA-E-restricted lymphocytes expressing NKG2A/C and/or CD107a, such as COPAXONE®, GLATOPA®, or BRABIO®, or generic forms or products thereof. In preferred embodiments, the patient has also been treated with an anti-HIV inhibitor, such as cART and each of the specific inhibitors described herein. The biological sample is preferably a blood sample, such as a PBMC (or other cell sample), plasma, or serum sample. RNA, DNA, or proteins can be prepared from the sample and the level of HIV-specific virus, DNA, RNA, or protein determined by well-known techniques in the art, such as PCR or other amplification reaction.

In various embodiments, In some embodiments, the biological sample comprises a body fluid sample such as a blood sample, serum sample, a plasma sample, or a depleted plasma sample, a semen sample, a sputum sample, an exudate. In some embodiments, the sample is obtained by blood draw. In some embodiments, the sample is obtained by finger-stick/prick or heel-prick. In some embodiments, the biological sample comprises an oral fluid sample. In some embodiments, the biological sample is a saliva sample. In some embodiments, the biological sample comprises cerebrospinal fluid or a tissue biopsy. In some embodiments, the biological sample comprises cells isolated from the subject (e.g., lymph node biopsy, immune cells, cells isolated from cheeks or gums). In some embodiments, the biological sample is not directly from a subject but is derived from or comprises cells grown and/or processed in vitro. In some embodiments, the biological sample comprises aqueous humour, vitreous humour, bile, breast milk, endolymph, perilymph gastric juice, mucus, peritoneal fluid, pleural fluid, sebum, semen, sweat, tears, vaginal secretion, vomit, or urine. In a preferred embodiment, the biological sample is a plasma sample or a concentrated virus sample.

In one embodiment, the biological sample is a blood sample, such as a whole blood, plasma, or serum sample. The biological sample can be from a patient infected with HIV-1 or HIV-2 and the patent can be chronically infected or acutely infected. The blood sample can be further separated into a "cell-free" (e.g. cell supernatant) biological sample and/or into a "cell pellet" biological sample, such as by centrifuging or filtering the biological sample.

In one embodiment, HIV virions are further separated and/or concentrated from the "cell-free" biological sample, for example by ultracentrifugation, with or without a substance to facilitate precipitation (e.g. polybrene). In one embodiment, the "cell-free" biological sample and/or virion biological sample can be lysed to release viral RNA and/or proteins from the virions, such as with a detergent or denaturant.

In one embodiment, viral proteins are extracted and/or purified, either together or individually, from the biological sample (e.g., cells, plasma, serum, virions etc.). In one embodiment, viral RNA is extracted and/or purified from the biological sample (e.g., cells, plasma, serum, virions etc.). In one embodiment, viral DNA is extracted and/or purified from the biological sample (e.g., cells, plasma, serum, virions etc.).

In one embodiment, the extracted and/or purified viral proteins are detected, such as by binding with a specific antibody, such as anti-HIV-1 and/or HIV-2 polyclonal and monoclonal antibodies that are readily available in the art. The antibody can be directly or indirectly labeled, such as with an enzymatic, radioactive, or fluorescent label. Such assays include ELISA, Western Blot, Multiplex, SIMOA, and similar assays.

In various embodiments, extracted and/or purified viral proteins are detected by mixing with beads comprising one or more molecules that specifically bind to a viral protein (e.g. p24 protein), and detecting the presence of and/or quantitating the viral protein (e.g. p24 protein) that is bound to the beads as a measure of the viral protein (e.g. p24 protein) that is present in the sample. Some of the methods of the invention comprise mixing a biological sample with an acidic solution to dissociate viral (e.g. p24) containing immune complexes that might be present in the biological sample, neutralizing the resulting mixture after a period of immune complex dissociation (ICD), contacting the neutralized resulting mixture with beads comprising one or more molecules that specifically bind p24, and detecting the presence of and/or quantitating the viral (e.g. p24) protein that is bound to the beads as a measure of the viral (e.g. p24) protein that is present in the sample. The mixing of an acidic solution with a biological sample (i.e., the acidification of the biological sample) is intended to result in a mixture having a pH between 1.0 and 5.9, between 2.0 and 5.0, between 2.2 and 4.0, between 2.5 and 3.0. The step of "neutralizing the resulting mixture" comprises the addition of a solution of basic pH (i.e., the "neutralizing solution") to the resulting mixture so as to increase its pH to a pH 6.0 or 6.5, to a neutral pH, to a pH of 6.5 to 7.0, to a pH of 7.0 to 7.5, to a pH of 7.5 to 8.0, to a pH of 8.0 to 8.5, to a pH of 8.5 to 9.0, to a pH of 9.0 to 11.0, or from a pH of 11.0 to 14.0.

In some embodiments, the beads are magnetic. In some embodiments, the beads are not magnetic. In some embodiments, the beads are paramagnetic. In some embodiments, the beads average diameter from about 0.1 micrometers to about 100 micrometers, from about 0.1 to about 10 micrometers, from about 0.1 to about 1 micrometer, from about 1 to 10. In a preferred embodiment, the beads average diameter is from about 1 micrometer to about 3 micrometers.

In some embodiments, the beads are of sphere-like shapes. In some embodiments, the beads are disks. In some embodiments, the beads are rings. In some embodiments, the beads have cube-like shapes. In some embodiments, the beads have a combination of shapes.

In some embodiments, the beads are made from materials selected from plastics or synthetic polymers (e.g., polyethylene, polypropylene, polystyrene, polyamide, polyurethane, phenolic polymers, or nitrocellulose etc.), naturally derived polymers (latex rubber, polysaccharides, polypeptides, etc), composite materials, ceramics, silica or silica-based materials, carbon, metals or metal compounds (e.g., comprising gold, silver, steel, aluminum, copper, etc.), inorganic glasses, silica, or a combination thereof.

In some embodiments, the beads are partially (e.g., 1%, 5%, 20%, 30%, 40%, 50%, 60%, 70%, 80%, 90%, 95%, or any values or ranges in between) coated by or conjugated to another material. In some embodiments, the beads are completely or about completely coated by or conjugated to another material. In some embodiments, the beads are coated by or conjugated to p24-binding molecule(s). In some embodiments, the coating or conjugation are done directly. In some embodiments, the coating or conjugating are indirect (e.g., there is another intermediate molecule between the beads and the p24-binding molecule). In some embodiments, the beads are coated or conjugated to p24-binding molecules of a single type. In some embodiments, there is more than one type of p24-binding molecule on the beads.

In some embodiments, the beads have approximately 250,000 p24-binding sites per bead or fewer. In some embodiments, the beads have between 50,000 and 300,000 binding sites per bead. In some embodiments, the beads have between 5,000 and 50,000 p24-binding sites per bead. In some embodiments, the beads comprising the p24-binding can be prepared by means described in, for example, U.S. patent application Ser. No. 12/731,130, entitled "Ultra-Sensitive Detection of Molecules or Particles using Beads or Other Capture Objects" by Duffy et al., filed Mar. 24, 2010; and International. Patent Application No. PCT/US11/026645, entitled "Ultra-Sensitive Detection of Molecules or Particles using Beads or Other Capture Objects" by Duffy et al., filed Mar. 1, 2011, each herein incorporated by reference).

In one embodiment, the extracted and/or purified viral DNA is detected. The viral DNA can be integrated or non-integrated into the host genome. Preferably, the viral DNA is detected by an amplification method, as described herein.

In one embodiment, the extracted and/or purified viral RNA is detected. The viral RNA can be either intracellular or extracellular, for example from a "cell-free" supernatant or concentrated virions. Preferably, the RNA is extracted and/or purified viral RNA from a human plasma sample or from a concentrated virus sample.

In various embodiments, the level of HIV RNA (e.g., in plasma) in the human can be measured by a reverse transcription and amplification reaction. For example, reverse transcription of the RNA of an HIV can be performed with a "reverse primer" specific for HIV. A "reverse primer" is one that, based on its 5'-3' orientation, can bind to a single-stranded RNA and serve to initiate generation of a complementary DNA (cDNA) copy of the RNA. The reverse transcription can be accomplished using well known and routine methods. The reaction mix for reverse transcription contains the reagents for the reaction, for example, a reverse primer, dNTPs (dATP, dCTP, dGTP and dTTP), a buffer, and a reverse transcriptase. Exemplary reaction conditions are set forth in the examples.

Amplification of the cDNA copy of an HIV generated by reverse transcription can be performed with a "forward primer" specific for HIV. A "forward primer" is one that, based on its 5'-3' orientation, can bind to a single-stranded antisense cDNA copy of an RNA generated by reverse transcription and serve to initiate generation of a double-stranded DNA copy of the RNA. The amplification can be accomplished using well known and routine methods. The reagent mix for amplification contains the reagents for the reaction, for example a forward primer, a reverse primer, dNTPs, a buffer, and a DNA polymerase.

In one embodiment, the method of the invention is performed using a single RT-PCR reagent mix containing the reagents for the reverse transcription and amplification reactions. Preferably, the reverse primer used for the reverse transcription reaction is also used for the amplification reaction.

Preferably, the reverse transcription and amplification reactions are performed in a plastic or glass container, most preferably in the same container.

Amplification methods known in the art include RCA, MDA, NASBA, TMA, SDA, LCR, b-DNA, PCR (all forms including RT-PCR), RAM, LAMP, ICAN, SPIA, QB-replicase, or Invader. A preferred amplification method is the polymerase chain reaction (PCR) amplification. See, e.g., PCR Technology: Principles and Applications for DNA Amplification (Ed. H. A. Erlich, Freeman Press, NY, N.Y., 1992); PCR Protocols: A Guide to Methods and Applications (Eds. Iinis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675. More preferred PCR methods is real-time PCR, PCR-HRM (High-Resolution DNA Melting) (see Andriantsoanirina et al. Journal of Microbiological Methods, 78: 165 (2009)) and PCR coupled to ligase detection reaction based on fluorescent microsphere (Luminex® microspheres).

Amplification techniques include in particular isothermal methods and PCR-based techniques. Isothermal techniques include such methods as nucleic acid sequence-based amplification (NASBA), loop-mediated isothermal amplification (LAMP), helicase-dependent amplification (HDA), rolling circle amplification (RCA), and strand displacement amplification (SDA), exponential amplification reaction (EXPAR), isothermal and chimeric primer-initiated amplification of nucleic acids (ICANs), signal-mediated amplification of RNA technology (SMART) and others (see e.g. Asiello and Baeumner, Lab Chip; 11(8): 1420-1430, 2011).

Preferably, the PCR technique quantitatively measures starting amounts of DNA, cDNA, or RNA. Examples of PCR-based techniques according to the invention include techniques such as, but not limited to, quantitative PCR (Q-PCR), reverse-transcriptase polymerase chain reaction (RT-PCR), quantitative reverse-transcriptase PCR (QRT-PCR), or digital PCR. These techniques are well known and easily available technologies for those skilled in the art.

Preferably, the method is a one-step real-time RT-PCR assay, for example, as described in the Examples. Most preferably, the method is a one-step real-time RT-PCR assay based on TAQMAN probe technology capable of detecting the recently described African E and F genogroups and including a competitive RNA internal control (IC), for example, as described in the Examples.

Preferably, a probe is used to detect the amplified product. The probe can be labeled with a fluorescent, radioactive, or enzymatic label. The amplified product can be detected with a specific detection chemistry such as fluorescence resonance energy transfer (FRET) probes, TAQMAN probes, molecular beacons, scorpion probes, fluorescently labeled (or other labeled) primers, lightup probes or a dye-based chemistry, DNA, PNA, LNA, or RNA including modified bases that bind to the amplified product to detect the sequence of interest.

Detection of the amplified products can be real-time (during the amplification process) or endpoint (after the amplification process). The invention allows for detection of the amplification products in the same vessel as amplification occurs.

Preferably, a DNA internal control is used to monitor the amplification reaction.

Preferably, a RNA internal control is used to monitor the reverse transcription and amplification reactions.

In some embodiments, the HIV virus in the sample is concentrated. The virus sample can be lysed to release the viral RNA.

A cell sample, such as a T cell, lymph node, gut or PBMC sample, can be lysed to release viral RNA, DNA, or protein.

In some embodiments, the compound (e.g., glatiramer acetate) is administered in at least one administration of 1-200 mg, 5-160 mg, 10-80 mg, or 20-40 mg. Preferably, the administration is at least 1-5, 5-10, 10-20, 20-40, 40-60, 60-80, 80-100, 100-120, 120-140, or 140-160 mg. Preferably, the administration is at least 1, 5, 10, 20, 40, 60, 80, 100, 120, 140, or 160 mg of the compound. Most preferably, the administration is at least 1, 5, 10, 20, 40, 60, 80, 100, 120, 140, or 160 mg of glatiramer acetate. Although not specifically enumerated, all values and subranges within the above and below ranges are specifically included as if explicitly written out.

The administration of the compound can be by many methods known in the art, most preferably subcutaneous, sublingual, transmucosal, or oral. See US20150202247A1, US20160193276A1, US20170080044A1, US20100036092A1, US20110066112A1, US20120015891A1, and US20150328277A1, all of which are incorporated by reference in their entirety.

In some embodiments, multiple administrations are given. In various embodiments, at least 1-100, preferably 1, 2, 3, 4, 5, 6, 7, 8, 9, 10-20, 20-50, or 50-100, administrations are given. In various embodiments, the administration is at least twice/day, twice/week, once/day, once/week, three times/week, or once/every 2 days.

In various embodiments, at least 1, 2, 5, 10, 15, 20, 25, 30, 35, 40, 45, 50, 55, 60, 65, 70, 75, 80, 100, 120, 160 mg/day is administered for at least 1, 2, 3, 4, 5, 6, 7 days, 1, 2, 3, 4, 5, 6 weeks, or 1, 2, 3, 4, 5, 6, etc. months.

In various embodiments, at least 1, 2, 5, 10, 15, 20, 25, 30, 35, 40, 45, 50, 55, 60, 65, 70, 75, 80, 100, 120, 160 mg is administered every 2 days or 3 times/week for at least 2, 3, 4, 5, 6, 7 days, 1, 2, 3, 4, 5, 6 weeks, or 1, 2, 3, 4, 5, 6, etc. months.

In one embodiment, the method comprises administering a dose of glatiramer acetate, such as COPAXONE®, GLATOPA®, or BRABIO®, or generic forms or products thereof, to a human, taking a biological sample (e.g., blood) from the human, preparing protein, RNA, or DNA from the biological sample, and measuring the level of HIV-specific protein, RNA, or DNA in the human. In a further embodiment, the method comprises taking a second biological sample (e.g., blood) from the human (preferably 1, 2, 3, or 4 months before or after the first sample), preparing protein, RNA, or DNA from the biological sample, and measuring the level of HIV-specific protein, RNA, or DNA in the human. In one embodiment, the method comprises providing a biological sample (e.g., blood) from an HIV-infected patient treated with at least one dose of glatiramer acetate, such as COPAXONE®, GLATOPA®, or BRABIO®, or generic forms or products thereof, optionally also treated with an anti-HIV inhibitor, such as cART and/or each of the specific inhibitors described herein, from the human, preparing protein, RNA, or DNA from the biological sample, and measuring the level of HIV-specific protein, RNA, or DNA in the human. In a further embodiment, the method comprises providing a second biological sample (e.g., blood) from the human (preferably taken 1, 2, 3, or 4 months before or after the first sample), preparing protein, RNA, or DNA from the biological sample, and measuring the level of HIV-specific protein, RNA, or DNA in the human.

Thus, the following methods are encompassed by the invention:

A method for detecting the presence or absence of HIV-specific nucleic acid comprising:
  a) administering a dose of glatiramer acetate to an HIV-infected patient;
  b) taking a blood sample from the patient;
  c) preparing RNA from the blood sample;
  d) preparing cDNA from the RNA;
  e) amplifying the cDNA by making DNA or RNA copies thereof to generate an amplified sample; and
  f) detecting the presence or absence of HIV-specific nucleic acid in the amplified sample.

A method for detecting the presence or absence of HIV-specific nucleic acid comprising:
  a) providing a blood sample from an HIV-infected patient treated with at least one dose of glatiramer acetate;
  b) preparing RNA from the blood sample;
  c) preparing cDNA from the RNA;
  d) amplifying the cDNA by making DNA or RNA copies thereof to generate an amplified sample; and
  e) detecting the presence or absence of HIV-specific nucleic acid in the amplified sample.

In some preferred embodiments of the above methods, HIV is HIV-1.

Any of these methods, wherein the method is repeated at least 2, 3, 4, 5, 6, 7, or more times. Thus, the invention encompasses the following method:

A method for detecting the presence or absence of HIV-specific nucleic acid comprising:
  a) providing a blood sample from an HIV-infected patient treated with at least one dose of glatiramer acetate;
  b) preparing RNA from the blood sample;
  c) preparing cDNA from the RNA;
  d) amplifying the cDNA or by making DNA or RNA copies thereof to generate an amplified sample;
  e) detecting the presence or absence of HIV-specific nucleic acid in the amplified sample;
  f) providing a second blood sample from the patient;
  g) preparing RNA from the blood sample in step f);
  h) preparing cDNA from the RNA in step g);
  i) amplifying the cDNA of step h) by making DNA or RNA copies thereof; and
  j) detecting the presence or absence of HIV-specific nucleic acid in the amplified sample of step i).

In some preferred embodiments of the above methods, HIV is HIV-1.

Any of these methods, wherein the method comprises making DNA copies of HIV-1 cDNA with the polymerase chain reaction (PCR), preferably with a real-time RT-PCR.

Any of these methods, wherein the method comprises making RNA copies of HIV-1 cDNA with T7 polymerase.

Any of these methods, wherein the method comprises detecting the presence or absence of HIV-1-specific nucleic acid in the amplified sample with a fluorescent label.

Any of these methods, wherein the HIV-1-infected patient has been treated with an anti-HIV inhibitor, such as cART and each of the specific inhibitors described herein. In various embodiments, the HIV-1-infected patient has been administered an anti-HIV inhibitor within 1, 2, 3, 4, 5, or 6 days, 1, 2, or 3 weeks, or 1, 2, 3, 4, 6, or 12 months prior to or after being administered at least one dose of glatiramer acetate.

Any of these methods, wherein the patient has never been diagnosed with multiple sclerosis.

Any of these methods, wherein the patient has never been diagnosed with HIV-1 associated cognitive impairment.

In a preferred embodiment, the cells in the blood sample are removed to generate a plasma sample and RNA is prepared from the plasma sample. In one embodiment, the plasma sample is subjected to ultracentrifugation prior to preparing RNA. In one embodiment, cDNA is prepared using oligo dT or an HIV-1-specific primer and a reverse transcriptase. In one embodiment, the cDNA is amplified using the polymerase chain reaction. In one embodiment, the HIV-1-specific nucleic acid is detected using a labeled (preferably fluorescent) probe or primer.

In one embodiment, the COBAS® HIV-1 Test, COBAS® AMPLISCREEN HIV-1 Test, COBAS® AMPLIPREP/COBAS® TAQMAN® HIV-1 Test, AMPLICOR HIV-1 MONITOR Test COBAS® TaqScreen MPX Test, or similar test is used. In one embodiment, the use of dual-labeled fluorescent probes allows for real-time detection of PCR product accumulation by monitoring of the emission intensity of fluorescent reporter dyes released during the amplification process.

In one embodiment, the NUCLISENS® HIV-1 QT Test or similar test is used. Multiple copies of each RNA target sequence are synthesized by T7-RNA polymerase by means of an intermediate DNA molecule that contains a double-stranded T7-RNA polymerase promoter. The DNA intermediate is generated through a process that involves the binding of a primer to the RNA template, the extension of primer by Reverse Transcriptase to form an RNA-DNA duplex, the degradation of the RNA strand of the duplex by RNase H, the binding of a second primer to the remaining DNA strand and, finally, the extension of the second primer to form the double-stranded T7-RNA polymerase promoter needed for transcription.

In one embodiment, the ABBOTT REALTIME HIV-1 ASSAY or similar test is used.

In one embodiment, the VERSANT HIV-1 RNA 3.0 Assay (bDNA) or similar test is used.

In one embodiment, the APTIMA® HIV-1 RNA Qualitative Assay, APTIMA® HIV-1 Quant Assay, PROCLEIX® HIV-1/HCV ASSAY, PROCLEIX ULTRIO ASSAY, or similar test is used. Plasma is treated with a detergent to solubilize the viral envelope, denature proteins and release viral genomic RNA. During sample preparation, RNA is isolated from plasma specimens via the use of target capture. Oligonucleotides ("capture oligonucleotides") that are homologous to highly conserved regions of HIV-1 are hybridized to the HIV-1 target, if present, in the test specimen. The hybridized target is then captured onto magnetic microparticles that are separated from plasma in a magnetic field. Wash steps are utilized to remove extraneous plasma components from the reaction tube. Target amplification occurs via TMA, which utilizes two enzymes, MMLV reverse transcriptase and T7 RNA polymerase. The reverse transcriptase is used to generate a DNA copy (containing a promoter sequence for T7 RNA polymerase) of the target RNA sequence. T7 RNA polymerase produces multiple copies of RNA amplicon from the DNA copy template.

Thus, the invention encompasses a method for detecting the presence or absence of HIV-1-specific nucleic acid comprising providing a biological sample from an HIV-1-infected patient treated with at least one dose of glatiramer acetate, and detecting the presence or absence of HIV-1-specific nucleic acid in the biological sample using the COBAS® HIV-1 Test, COBAS® AMPLISCREEN HIV-1 Test, COBAS® AMPLIPREP/COBAS® TAQMAN® HIV-1 Test, AMPLICOR HIV-1 MONITOR Test, COBAS® TaqScreen MPX Test, NUCLISENS® HIV-1 QT Test, VERSANT HIV-1 RNA 3.0 Assay (bDNA), ABBOTT REAL-TIME HIV-1 ASSAY, APTIMA® HIV-1 RNA Qualitative Assay, APTIMA® HIV-1 Quant Assay, PROCLEIX ULTRIO ASSAY, PROCLEIX HIV-1/HCV ASSAY, or a similar test.

Copies of the manuals for each of these HIV-1 NAT test kits are available from FDA at Fda.gov (/BiologicsBlood-Vaccines/BloodBloodProducts/ApprovedProducts/LicensedProductsBLAs/BloodDonorScreening/InfectiousDisease/ucm126582.htm), and are hereby incorporated by reference.

Treatment Methods and Uses

The invention encompasses methods of treatment using glatiramer acetate and GA related active substances and products and the use of compositions comprising glatiramer acetate and GA related active substances and products in the treatment of an HIV infection in a human patient.

Figure 3:
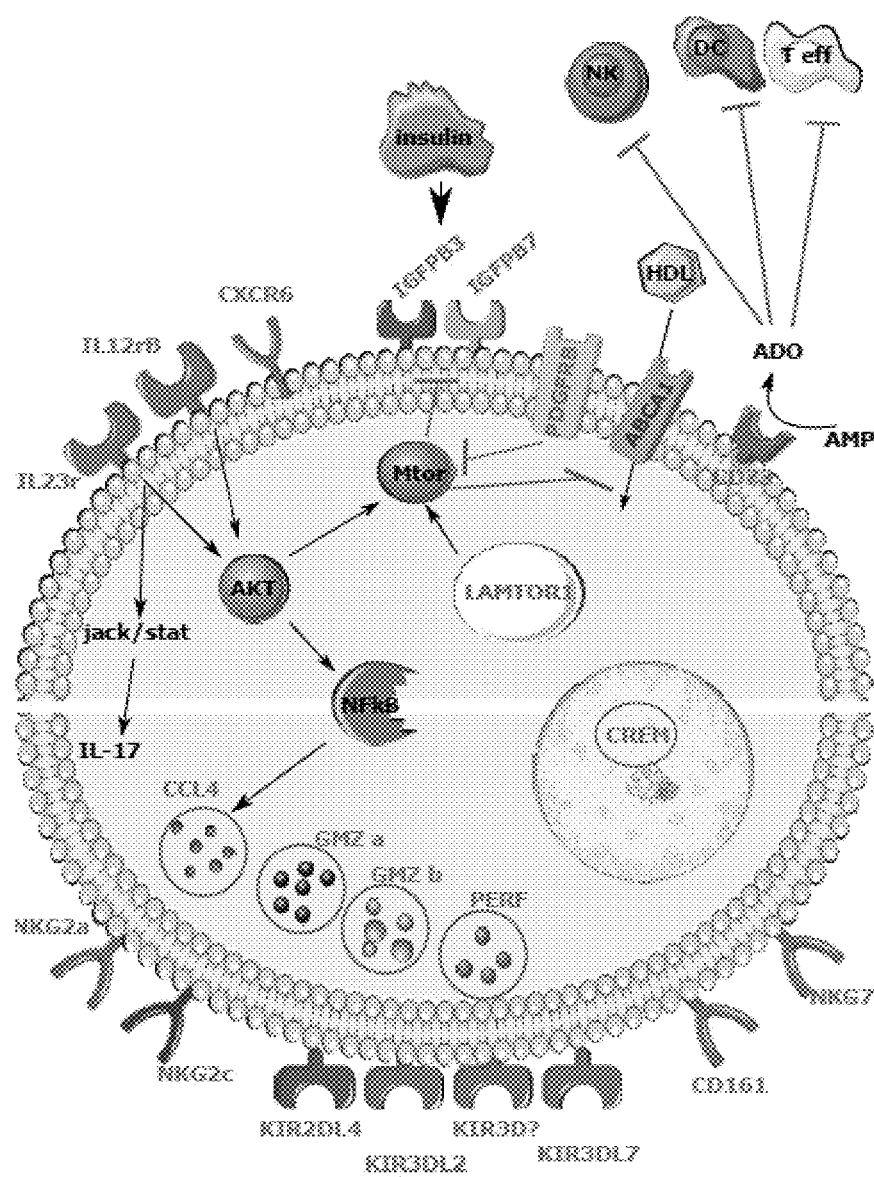
FIG. 3: Molecular profiling of the MHC-E restricted CD8 T cells in AGM. RNAseq analysis was performed on 3 distinct CD8 T cell populations from four animals. The molecules in bold depict examples of those genes whose expression was increased specifically in MHC-E restricted CD8 T cells, those down-regulated are not shown except for LAMTOR1. The other molecules shown are belonging to the corresponding signaling pathways.

The invention encompasses a compound inducing activation of HLA-E-restricted CD8 cells and/or NK cells in a human subject, for use to treat HIV infection. More specifically, it relates to a compound inducing activation of HLA-E-restricted CD8 cells and/or NK cells which are expressing NKG2A/C and/or CD107a in the treatment of an HIV infection in a human patient. More specifically, GA induces HLA-E-restricted CD8 cells which harbor NK cells markers as indicated in FIG. 3, such as at least two biomarkers selected from NKG2A, NKG2C, KIR receptors such as KIR2DL4, KIR3DL2, KIR3D, KIR3DL7, as well as CD161, and NKG7. NK cells induced by GA have NK cells markers such as those shown in FIG. 12.

The compound can be Glatiramer acetate (GA) for use in treating HIV infected human subjects and adminstered to patients undergoing cART or in HIV patients which never initiated cART.

In one embodiment, GA is L-glutamic acid polymer with L-alanine, L-lysine and L-tyrosine, acetate (salt) of formula: (Glu,Ala,Lys,Tyr)x.X.CH3COOH, such as GA as described as CAS-147245-92-9. For example, GA consists of the acetate salts of synthetic polypeptides, containing L-glutamic acid, L-alanine, L-tyrosine, and L-lysine with an average molar fraction of 0.141, 0.427, 0.095, and 0.338, respectively. Preferably, GA is COPAXONE®, GLATOPA®, or BRADIO®, or generic forms or products thereof.

GA was initially known as copolymer-1 (Sela et al, 1996—Vaccine Volume 10, Issue 14, 1992, Pages 991-999) for immunomodulation properties in allergic encephalomyelitis in experimental animals, which led later to clinical trials and Market Authorization to treat patients suffering from exacerbating remitting multiple sclerosis. Still today, GA mechanism of action is not fully elucidated but it is postulated to have effects on adaptive and innate immune mechanisms. In addition, studies have shown equivalence of GA generic versions, such as Synthon BV's generic glatiramer acetate—Equivalence of Generic Glatiramer Acetate in Multiple SclerosisA Randomized Clinical Trial (JAMA Neurol. 2015; 72(12):1433-1441. doi:10.1001/jamaneurol.2015.2154 which is herein incorporated by reference). This equivalence and methods to prepare GA equivalent products or related substance or products is described in Anderson et al, J. of Neurological Sciences, 369 p 24-34, 2015 which is herein incorporated by reference.

The average molecular weight of glatiramer acetate is 4,700-11,000 daltons. Chemically, glatiramer acetate is designated Lglutamic acid polymer with L-alanine, L-lysine and L-tyrosine, acetate (salt). Its structural formula is: (Glu, Ala, Lys, Tyr) x. xCH3COOH.

In one specific embodiment, GA is COPAXONE® (Teva) as described in EP0975351A1 which consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. It is also referred to as poly [L-Glu13"15, L-Ala39"46, L-Tyr8-6"10, L-Lys30-37]. n CH3COOH. CopoLymer 1.

In one specific embodiment, GA is GLATOPA®—www.glatopa.com (Sandoz)—(Demonstration of equivalence of a generic glatiramer acetate (Glatopa™)—Anderson et al, J. of Neurological Sciences, 369 p 24-34, 2015.

In one specific embodiment, GA is Synthon BV's generic glatiramer acetate, now marketed under the name BRABIO® (Mylan), or any other bioequivalent generic GA.

In the context of the present invention, GA and GA related active substance or product are contemplated for treating HIV. GA related active substance or product are meant to have modifications in the final composition of the copolymer for example in the mean kDa in the relative proportions of amino acid in the copolymer with different arrangements of (Glu, Ala, Lys, Tyr) x; so long as it shows similar biological activities of GA as measured by any of the method set forth in the examples such as measuring NKG2A/C and/or CD107a expression in HLA-E restricted CD8 T cells and/or NK cells. Therefore, the invention embraces the use of marketed as COPAXONE® or GLATOPA® or another generic form thereof; and/or even GA related substances or products with properties to induce proliferation of HLA-E-restricted lymphocytes such as HLA-E-restricted CD8 T and/or NK cells cells which are NKG2A/C positive and/or CD107a positive as well as other biomarkers of HIV infection as explained herein.

The invention encompasses different forms of GA, chemically distinct GAs so long as it retains similar properties as discovered by the inventors to elicit HLA-E-restricted CD8 T cells and/or NK cells, which are NKG2A/C+ and/or CD107a+; and thereby achieve landmarks such as in the in the level of CD4 T lymphocytes compared to a baseline level, in the level of HIV RNA load in plasma compared to a baseline level, in the level of HIV DNA in plasma compared to a baseline level.

Therefore, the invention is directed to a compound for use as depicted above which is Glatiramer acetate related drug substance or product characterized by the process comprising the steps of:

administering a suitable amount of the Glatiramer acetate related drug substance, or drug product in a non human mammal, determining the activation level of HLA-E-restricted CD8 T cells and/or NK cells in said mammal compared to a baseline level, wherein an increase in activation of HLA-E-restricted T cells and/or NK cells, such as an increase of the number of HLA-E-restricted CD8 T and NK cells expressing NKG2A/C and/or expressing CD107a in said mammal characterizes said GA related substance or product as a product for treating HIV infection in humans.

In various embodiments, the invention is directed to a compound for use as depicted above which is a Glatiramer acetate related drug substance or product characterized by the processes described in the examples.

The GA or GA related products can be in the form of a product for subcutaneous injection, such as a product for subcutaneous injection which can be 1 mL prefilled syringe (PFS) of GA solution containing 20 mg or 40 mg of GA, the active ingredient, and 40 mg of mannitol. Such PFS can comprise an aqueous pharmaceutical solution having a pH in the range of 5.5-7.0. Alternatively, The GA or GA related products is in the form of nano or microparticles comprising from about 20 mg to about 1000 mg of glatiramer acetate or GA related active substance as defined herein. The GA or GA related products can also be in the form of a long acting parenteral pharmaceutical composition in sustained release depot form suitable for subcutaneous or intramuscular implantation at a medically acceptable location in a subject in need thereof. The GA or GA related products can also comprise biodegradable or non-biodegradable polymer selected from the group consisting of poly(D,L, lactic acid) (PLA), polyglycolides (PGA), poly(lactide-co-glycolide) (PLGA) polycaprolactone, polyhydroxybutyrate, polyorthoesters, polyalkaneanhydrides, gelatin, collagen, oxidized cellulose, and polyphosphazene.

In one embodiment, the invention is directed to the compound as depicted above for use in patients which are acutely or chronically infected with HIV. These patients may have previously undergone cART, and either cease or continue cART.

The administration of the compound as depicted above can be given at least twice/day, twice/week, once/day, once/week, three times/week, or once/every 2 days.

The administration of the compound as depicted above can be given at a dose of at least 10, 15, 20, 25, 30, 35, 40, 45, 50, 55, 60, 65, 70, 75, 80, 100, 120, or 160 mg.

In one other embodiment, the compound as depicted above can be administered in conjunction with an HIV inhibitor, for example in conjunction with at least 2 or 3 HIV inhibitors, such as in conjunction with cART.

Preferably, cART can be Combivir, Kaletra, Trizivir, Epzicom, Kivexa, Truvada, Atripla, Complera, Eviplera, Stribild, Triumeq, Evotaz, Prezcobix, Dutrebis, Genvoya, or Descovy.

More preferably, cART comprises at least 2 or 3 of any of the following compounds:
lamivudine; zidovudine; lopinavir; ritonavir; abacavir; tenofovir disoproxil fumarate; emtricitabine; efavirenz; rilpivirine; elvitegravir; cobicistat; dolutegravir; atazanavir; cobicistat; darunavir; and raltegravir. In some embodiments, the HIV inhibitor comprises a Rev inhibitor.

In one embodiment, the invention is directed to the compound as depicted above for use in patients which have never been diagnosed with Multiple sclerosis.

In one embodiment, the invention is directed to the compound as depicted above for use in patients which have never been diagnosed with HIV encephalopathy.

In one embodiment, the method comprises administering an effective amount of glatiramer acetate to an HIV-infected human. An effective amount is an amount of glatiramer acetate that reduces the level of plasma HIV RNA in the HIV-infected patient at least 2-fold. In some embodiments, the administration of glatiramer acetate reduces the level of plasma HIV RNA in the HIV-infected patient at least 2-, 4-, 10-, 30-, 50-, or 100-fold.

In some embodiments, the administration of glatiramer acetate reduces the viral load in the patient at least 2-, 4-, 10-, 30-, 50-, or 100-fold. In some embodiments, the administration of glatiramer acetate reduces the number infected reservoir cells at least 2-, 4-, 10-, 30-, 50-, or 100-fold. In some embodiments, the administration of glatiramer acetate reduces active viral replication at least 2-, 4-, 10-, 30-, 50-, or 100-fold.

The above reductions can be determined by routine techniques in the art, such as by comparing the levels in the patient before and after administration of glatiramer acetate, for example by standard PCR amplification methods with patient plasma samples.

The reduction can be assessed at various times after administration, for example at 1, 2, 3, 4, 5, 6, 7, 8, 9, 10, 11, 12, 16, 20, 40, or 52 weeks after administration of glatiramer acetate.

In some embodiments, the compound (e.g., glatiramer acetate) is administered in at least one administration of 1-200 mg, 5-160 mg, 10-80 mg, or 20-40 mg. Preferably, the administration is at least 1-5, 5-10, 10-20, 20-40, 40-60, 60-80, 80-100, 100-120, 120-140, or 140-160 mg. Preferably, the administration is at least 1, 5, 10, 20, 40, 60, 80, 100, 120, 140, or 160 mg of the compound. Most preferably, the administration is at least 1, 5, 10, 20, 40, 60, 80, 100, 120, 140, or 160 mg of glatiramer acetate. Although not specifically enumerated, all values and subranges within the above and below ranges are specifically included as if explicitly written out.

The administration of the compound can be by many methods known in the art, most preferably subcutaneous, sublingual, transmucosal, or oral. See US20150202247A1, US20160193276A1, US20170080044A1, US20100036092A1, US20110066112A1, US20120015891A1, and US20150328277A1, all of which are incorporated by reference in their entirety.

In some embodiments, multiple administrations are given. In various embodiments, at least 1-100, preferably 1, 2, 3, 4, 5, 6, 7, 8, 9, 10-20, 20-50, or 50-100, administrations are given. In various embodiments, the administration is at least twice/day, twice/week, once/day, once/week, three times/week, or once/every 2 days.

In various embodiments, at least 1, 2, 5, 10, 15, 20, 25, 30, 35, 40, 45, 50, 55, 60, 65, 70, 75, 80, 100, 120, 160 mg/day is administered for at least 1, 2, 3, 4, 5, 6, 7 days, 1, 2, 3, 4, 5, 6 weeks, or 1, 2, 3, 4, 5, 6, etc. months.

In various embodiments, at least 1, 2, 5, 10, 15, 20, 25, 30, 35, 40, 45, 50, 55, 60, 65, 70, 75, 80, 100, 120, 160 mg is administered every 2 days or 3 times/week for at least 2, 3, 4, 5, 6, 7 days, 1, 2, 3, 4, 5, 6 weeks, or 1, 2, 3, 4, 5, 6, etc. months.

HIV-Infected Patients

The methods, uses, and compositions of this invention can be used with HIV-infected patients. In one embodiment, the patient is infected with Human Immunodeficiency Virus type 1 (HIV-1). In one embodiment, the patient is infected with Human Immunodeficiency Virus type 2 (HIV-2).

In one embodiment, the HIV-1 infected patient is acutely infected with HIV. In one embodiment, the HIV-1 infected patient is chronically infected with HIV.

In one embodiment, the HIV-1 infected patient is undergoing cART. In one embodiment, the HIV-1 infected patient has never initiated cART. In various embodiments, the HIV-1 infected patient has previously undergone cART, and either ceases or continues cART.

In some embodiments, the patient has never been diagnosed with multiple sclerosis.

In some embodiments, the patient has never been diagnosed with HIV-1 associated cognitive impairment.

Pharmaceutical Compositions

The invention encompasses pharmaceutical compositions that increase HLA-E-restricted lymphocytes such as CD8 T cells and/or NK cells in a Human Immunodeficiency Virus-infected patient. Preferred pharmaceutical compositions comprise a HIV inhibitory amount of glatiramer acetate. The compositions are preferably for the treatment of an HIV infection in a human, particularly by increasing HLA-E-restricted CD8 T cells and/or NK cells, preferably in combination with at least one, two, three, or four HIV inhibitors, most preferably in combination with cART. The invention further encompasses the use of these compositions in the manufacture of a medicament for the treatment of an HIV infection and the use of these compositions in the treatment of an HIV infection.

Preferred pharmaceutical compositions include the compositions set forth in US20150202247A1, US20160193276A1, US20170080044A1, US20100036092A1, US20110066112A1, US20120015891A1, and US20150328277A1, all of which are incorporated by reference in their entirety.

In various embodiments, the compound contains 1-200 mg, 5-160 mg, 10-80 mg, or 20-40 mg of glatiramer acetate. Preferably, the compound contains at least 1-5, 5-10, 10-20, 20-40, 40-60, 60-80, 80-100, 100-120, 120-140, or 140-160 mg of glatiramer acetate. Preferably, the compound contains at least 1, 5, 10, 20, 40, 60, 80, 100, 120, 140, or 160 mg of the of glatiramer acetate. Although not specifically enumerated, all values and subranges within the above ranges are specifically included as if explicitly written out.

Glatiramer acetate may also be advantageously administered for therapeutic purposes together with HIV inhibitors, particularly cART, known in the general art to be of value in treating HIV infection. Particularly preferred combinations contain at least one, two, three, or four of the HIV inhibitors listed below. Most preferably, the combination contains at least one of the combination antiretroviral therapies listed below.

Effective concentrations or amounts of glatiramer acetate can be mixed with a suitable pharmaceutical carrier or vehicle for systemic, topical or local administration to form pharmaceutical compositions. Glatiramer acetate is included in an amount effective for treating HIV infection. The concentration of active agent in the composition will depend on absorption, inactivation, excretion rates of the active agent, the dosage schedule, amount administered, particular formulation as well as other factors known to those of skill in the art.

The compositions are intended to be administered by a suitable route, including by way of example and without limitation orally, parenterally, rectally, topically and locally. For oral administration, capsules and tablets can be used. The compositions are in liquid, semi-liquid or solid foul and are formulated in a manner suitable for each route of administration.

Solutions or suspensions used for parenteral, intradermal, subcutaneous, or topical application can include any of the following components, in any combination: a sterile diluent, including by way of example without limitation, water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampoules, disposable syringes or single or multiple dose vials made of glass, plastic or other suitable material.

In instances in which the agents exhibit insufficient solubility, methods for solubilizing agents may be used. Such methods are known to those of skill in this art, and include, but are not limited to, using co-solvents, such as dimethylsulfoxide (DMSO), using surfactants, such as TWEEN®, or dissolution in aqueous sodium bicarbonate. Pharmaceutically acceptable derivatives of the agents may also be used in formulating effective pharmaceutical compositions.

Upon mixing or addition of the agent(s), the resulting mixture may be a solution, suspension, emulsion or the like. The form of the resulting mixture depends upon a number of factors, including the intended mode of administration and the solubility of the agent in the selected carrier or vehicle. The effective concentration is sufficient for treating one or more symptoms of at least one disease state.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the agents or pharmaceutically acceptable derivatives thereof. The pharmaceutically therapeutically active agents and derivatives thereof are typically formulated and administered in unit-dosage forms or multiple-dosage forms. Unit-dose foams as used herein refers to physically discrete units suitable for human and animal subjects and packaged individually as is known in the art. Each unit-dose contains a predetermined quantity of the therapeutically active agent sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active agent, for example and without limitation: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active agent as defined above and optional pharmaceutical adjuvants in a carrier, such as, by way of example and without limitation, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, such as, by way of example and without limitation, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active agent in an amount sufficient to alleviate the symptoms of the treated subject.

Dosage forms or compositions containing active agent in the range of 0.005% to 100% with the balance made up from non-toxic carrier may be prepared. For oral administration, a pharmaceutically acceptable non-toxic composition is formed by the incorporation of any of the normally employed excipients, such as, for example and without limitation, pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active agent, such as 0.1-85%, or such as 75-95% The active agents or pharmaceutically acceptable derivatives may be prepared with carriers that protect the agent against rapid elimination from the body, such as time release formulations or coatings. The compositions may include other active agents to obtain desired combinations of properties.

Oral pharmaceutical dosage forms include, by way of example and without limitation, solid, gel and liquid. Solid dosage forms include tablets, capsules, granules, and bulk powders. Oral tablets include compressed, chewable lozenges and tablets which may be enteric-coated, sugar-coated or film-coated. Capsules may be hard or soft gelatin capsules, while granules and powders may be provided in non-effervescent or effervescent forms with the combination of other ingredients known to those skilled in the art.

In some embodiments, the formulations are solid dosage forms, such as capsules or tablets. The tablets, pills, capsules, troches and the like can contain any of the following ingredients, or agents of a similar nature: a binder; a diluent; a disintegrating agent; a lubricant; a glidant; a sweetening agent; and a flavoring agent.

Examples of binders include, by way of example and without limitation, microcrystalline cellulose, gum tragacanth, glucose solution, acacia mucilage, gelatin solution, sucrose, and starch paste. Lubricants include, by way of example and without limitation, talc, starch, magnesium or calcium stearate, lycopodium and stearic acid. Diluents include, by way of example and without limitation, lactose, sucrose, starch, kaolin, salt, mannitol, and dicalcium phosphate. Glidants include, by way of example and without limitation, colloidal silicon dioxide. Disintegrating agents include, by way of example and without limitation, crosscarmellose sodium, sodium starch glycolate, alginic acid, corn starch, potato starch, bentonite, methylcellulose, agar and carboxymethylcellulose. Coloring agents include, by way of example and without limitation, any of the approved certified water soluble F1) and C dyes, mixtures thereof; and water insoluble ID and C dyes suspended on alumina hydrate. Sweetening agents include, by way of example and without limitation, sucrose, lactose, mannitol and artificial sweetening agents such as saccharin, and any number of spray dried flavors. Flavoring agents include, by way of example and without limitation, natural flavors extracted from plants such as fruits and synthetic blends of agents which produce a pleasant sensation, such as, but not limited to peppermint and methyl salicylate. Wetting agents include, by way of example and without limitation, propylene glycol monostearate, sorbitan monooleate, diethylene glycol monolaurate, and polyoxyethylene laural ether. Emetic-coatings include, by way of example and without limitation, fatty acids, fats, waxes, shellac, ammoniated shellac and cellulose acetate phthalates. Film coatings include, by way of example and without limitation, hydroxyethylcellulose, sodium carboxymethylcellulose, polyethylene glycol 4000 and cellulose acetate phthalate.

If oral administration is desired, the agent could be provided in a composition that protects it from the acidic environment of the stomach. For example, the composition can be formulated in an enteric coating that maintains its integrity in the stomach and releases the active agent in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The agents can also be administered as a component of an elixir, suspension, syrup, wafer, sprinkle, chewing gum or the like. A syrup may contain, in addition to the active agents, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics.

Pharmaceutically acceptable carriers included in tablets are binders, lubricants, diluents, disintegrating agents, coloring agents, flavoring agents, and wetting agents. Entericcoated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents may be used in any of the above dosage forms.

Solvents, include by way of example and without limitation, glycerin, sorbitol, ethyl alcohol and syrup. Examples of preservatives include without limitation glycerin, methyl and propylparaben, benzoic add, sodium benzoate and alcohol. Non-aqueous liquids utilized in emulsions, include by way of example and without limitation, mineral oil and cottonseed oil. Emulsifying agents, include by way of example and without limitation, gelatin, acacia, tragacanth, bentonite, and surfactants such as polyoxyethylene sorbitan monooleate. Suspending agents include, by way of example and without limitation, sodium carboxymethylcellulose, pectin, tragacanth, Veegum and acacia. Diluents include, by way of example and without limitation, lactose and sucrose. Sweetening agents include, by way of example and without limitation, sucrose, syrups, glycerin and artificial sweetening agents such as saccharin. Wetting agents, include by way of example and without limitation, propylene glycol monostearate, sorbitan monooleate, diethylene glycol monolaurate, and polyoxyethylene lauryl ether. Organic acids include, by way of example and without limitation, citric and tartaric acid. Sources of carbon dioxide include, by way of example and without limitation, sodium bicarbonate and sodium carbonate. Coloring agents include, by way of example and without limitation, any of the approved certified water soluble FD and C dyes, and mixtures thereof. Flavoring agents include, by way of example and without limitation, natural flavors extracted from plants such fruits, and synthetic blends of agents which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, for example in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active agent or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those containing an agent provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Tablets and capsules formulations may be coated as known by those of skill in the art in order to modify or sustain dissolution of the active ingredient. Thus, for example and without limitation, they may be coated with a conventional enterically digestible coating, such as phenylsalicylate, waxes and cellulose acetate phthalate.

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients, include by way of example and without limitation, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, glatiramer acetate can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The agent diffuses through the outer polymeric membrane in a release rate controlling step. The percentage of active agent contained in such parenteral compositions is highly dependent on the specific nature thereof, as well as the activity of the agent and the needs of the subject.

Parenteral administration includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Aqueous vehicles include, by way of example and without limitation, Sodium Chloride Injection, Ringers Injection, Isotonic Dextrose Injection, Sterile Water Injection, Dextrose and Lactated Ringers Injection. Nonaqueous parenteral vehicles include, by way of example and without limitation, fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include, by way of example and without limitation, sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include, by way of example and without limitation, ethyl alcohol, polyethylene glycol and propylene glycol for water miscible vehicles and sodium hydroxide, hydrochloric acid, citric acid or lactic acid for pH adjustment.

The concentration of the pharmaceutically active agent is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. Preparations for parenteral administration should be sterile, as is known and practiced in the art.

Illustratively, intravenous or intra-arterial infusion of a sterile aqueous solution containing an active agent is an effective mode of administration. Another embodiment is a sterile aqueous or oily solution or suspension containing an active agent injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active agent to the treated tissue(s). The active agent may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The agent may be suspended in micronized or other suitable form or may be derivatized, e.g., to produce a more soluble active product or to produce a prodrug or other pharmaceutically acceptable derivative. The form of the resulting mixture depends upon a number of factors, including the intended mode of administration and the solubility of the agent in the selected carrier or vehicle. The effective concentration is sufficient for ameliorating the symptoms of the condition and may be empirically determined.

Lyophilized powders can be reconstituted for administration as solutions, emulsions, and other mixtures or formulated as solids or gels.

The sterile, lyophilized powder is prepared by dissolving an agent provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain, by way of example and without limitation, a single dosage (10-1000 mg, such as 100-500 mg) or multiple dosages of the agent. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, such as about 5-35 mg, for example, about 9-30 mg of lyophilized powder, is added per mL of sterile water or other suitable carrier. The precise amount depends upon the selected agent. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The agents or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, by way of example and without limitation, have diameters of less than about 50 microns, such as less than about 10 microns.

The agents may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active agent alone or in combination with other pharmaceutically acceptable excipients can also be administered.

These solutions, particularly those intended for ophthalmic use, may be formulated, by way of example and without limitation, as about 0.01% to about 10% isotonic solutions, pH about 5-7, with appropriate salts.

Other routes of administration, such as transdermal patches, and rectal administration are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

Pharmaceutical dosage thin's for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (*theobroma* oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is, by way of example and without limitation, about 2 to 3 gm.

Tablets and capsules for rectal administration are manufactured using the same pharmaceutically acceptable substance and by the same methods as for formulations for oral administration.

Kit of Parts

The invention includes a kit of parts for simultaneous, separate, sequential administration to an HIV-infected patient. The kit can comprise any of the pharmaceutical compositions of the invention together with an HIV inhibitor.

The kit of parts can contain at least 1-200 mg, 5-160 mg, 10-80 mg, or 20-40 mg of glatiramer acetate. Preferably, the kit of parts contains at least 1-5, 5-10, 10-20, 20-40, 40-60, 60-80, 80-100, 100-120, 120-140, or 140-160 mg of glatiramer acetate. Preferably, the kit of parts contains at least 1, 5, 10, 20, 40, 60, 80, 100, 120, 140, or 160 mg of the of glatiramer acetate. Although not specifically enumerated, all values and subranges within the above ranges are specifically included as if explicitly written out.

Preferably, the kit of parts contains at least one, two, three, or four of the HIV inhibitors listed below. Most preferably, the kit of parts contains at least one of the combination antiretroviral therapies listed below.

HIV Inhibitors

Entry inhibitors (or fusion inhibitors) interfere with binding, fusion and entry of HIV-1 to the host cell by blocking one of several targets (Wikipedia). Maraviroc works by targeting CCR5, a co-receptor located on human helper T-cells. Enfuvirtide is a peptide drug that must be injected and acts by interacting with the N-terminal heptad repeat of gp41 of HIV to form an inactive hetero six-helix bundle, therefore preventing infection of host cells.

Nucleoside reverse transcriptase inhibitors (NRTI) and nucleotide reverse transcriptase inhibitors (NtRTI) are nucleoside and nucleotide analogues which inhibit reverse transcription. Examples of NRTIs include zidovudine, abacavir, lamivudine, emtricitabine, and tenofovir.

Non-Nucleoside reverse transcriptase inhibitors (NNRTI) inhibit reverse transcriptase by binding to an allosteric site of the enzyme. 1st generation NNRTIs include nevirapine and efavirenz. 2nd generation NNRTIs include etravirine and rilpivirine.

Integrase inhibitors (also known as integrase nuclear strand transfer inhibitors or INSTIs) inhibit the viral enzyme integrase. Integrase inhibitors include raltegravir, elvitegravir, and dolutegravir.

Protease inhibitors block the viral protease enzyme necessary to produce mature virions upon budding from the host membrane. Examples of HIV protease inhibitors are lopinavir, indinavir, nelfinavir, amprenavir, ritonavir, darunavir, and atazanavir.

Maturation inhibitors have a similar effect by binding to gag, and include bevirimat and vivecon.

Combination antiretroviral therapy (cART) is a mixture of at least two, and preferably three or more different classes of antiretroviral therapy. All different combinations of the antiretroviral therapies specified herein are specifically contemplated. Examples of cART include:

Combivir: lamivudine+zidovudine.
Kaletra: lopinavir+ritonavir
Trizivir: abacavir+lamivudine+zidovudine
Epzicom (in USA)/Kivexa (in Europe and Russia): abacavir+lamivudine.
Truvada: tenofovir disoproxil fumarate+emtricitabine.
Atripla: emtricitabine+tenofovir disoproxil fumarate+efavirenz
Complera (in USA)/Eviplera (in Europe and Russia): emtricitabine+rilpivirine+tenofovir disoproxil fumarate.
Stribild: elvitegravir+cobicistat+emtricitabine+tenofovir disoproxil fumarate.
Triumeq: abacavir+dolutegravir+lamivudine.
Evotaz: atazanavir+cobicistat.
Prezcobix: darunavir+cobicistat.
Dutrebis: lamivudine+raltegravir.
Genvoya: elvitegravir+cobicistat+emtricitabine+tenofovir alafenamide fumarate.
Descovy: emtricitabine+tenofovir alafenamide fumarate.

Rev inhibitors interfere with the biogenesis of viral RNA required for the replication of HIV. Rev inhibitor can function through binding to the Cap Binding Complex at the 5' end of the mRNA coding for 3 structural proteins of the virus. By promoting HIV RNA splicing, these inhibitors can reduce the level of genomic RNA and inhibit HIV replication.

Preferred compounds can be found in U.S. Pat. Nos. 9,145,367 and 9,061,999, which are hereby incorporated by reference. Particularly preferred compounds are 10-chloro-2,6-dimethyl-2H-pyrido [3',4':4,5]pyrrolo[2,3-g]isoquinoline (IDC16), 8-chloro-N-(4-(trifluoromethoxy)phenyl)quinolin-2-amine (ABX464) and 8-chloro-N-glucuronide-N-(4-(trifluoromethoxy)phenyl)quinolin-2-amine) (ABX464-N-glucuronide) compounds, as set forth in Campos et al. Retrovirology (2015) 12:30, which is hereby incorporated by reference.

A particularly preferred compound has the formula:

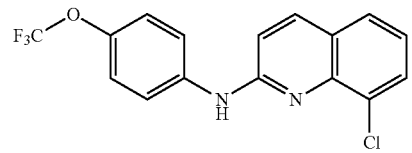 [SMILES: FC(F)(F)Oc1ccc(Nc2ccc3cccc(Cl)c3n2)cc1]

In the various embodiments of the above compositions, methods and uses, the compound may induce activation and/or increase of HLA-E restricted CD8 T cells expressing one or more of NK cell markers, homing-receptors, cytokine receptors, and/or effector phenotype markers disclosed in the examples and figures.

EXAMPLES

HLA-E Restricted CD8 T Cells Increase in Non-Pathogenic SIV-Infections

Figure 1B:
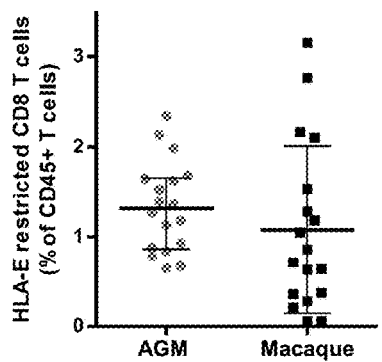
Figure 1C:
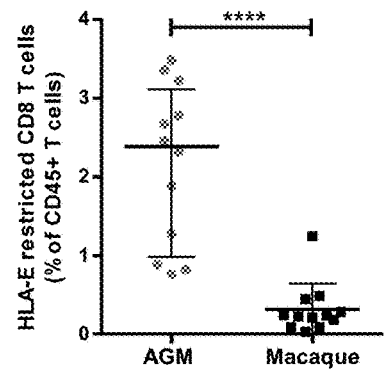
Figure 2A:
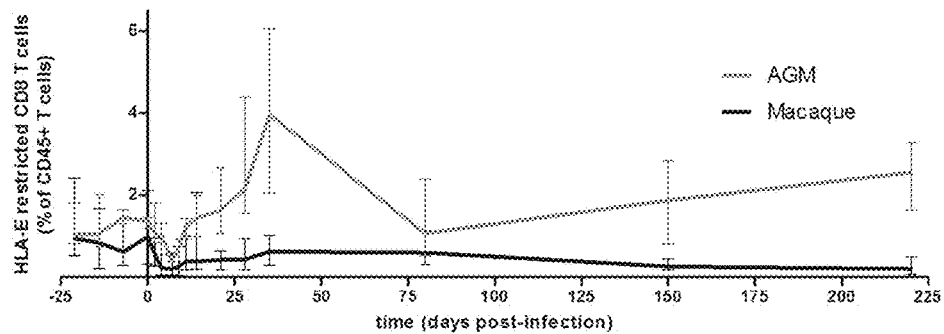
FIG. 2A-C: Follow-up of the percentage of MHC-E restricted CD8 T cells among lymphoid cells (CD45+) during SIV infection in the blood (FIG. 2A), lymph nodes (FIG. 2B) and rectal biopsies (FIG. 2C) of 6 AGM and 6 macaques by flow cytometry. Data are presented as medians and interquartile ranges.
Figure 2B:
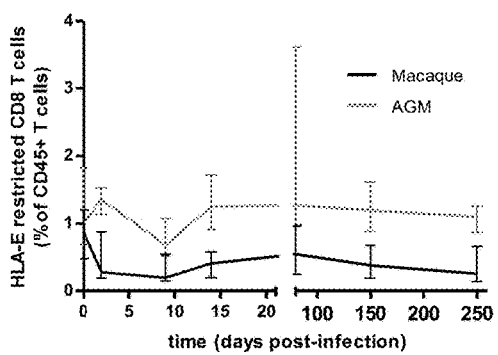

In order to search for the factors responsible for the protection against AIDS in AGM, we compared the immune responses during non-pathogenic SIV infection in AGM to those in pathogenic infection in macaques. In total 12 animals were followed. We discovered that HLA-E restricted CD8 T cells expand in response to SIV infection in AGM (FIG. 1 and FIG. 2). In contrast to AGM, very low levels of these cells were observed in chronically SIV infected macaques, whereas similar levels were found in healthy animals in both species (FIG. 1).

Phenotypic and Molecular Markers of HLA-E Restricted CD8 T Cells

We characterized the phenotype of these cells from the 12 animals by multi-color flow cytometry. This revealed that these HLA-E restricted CD8 T cells are of the effector phenotype. Moreover, they showed several characteristics: expression of NK cell-like markers (such as NKG2A and NKp80); homing receptors (such as CXCR3, CD161, CCR7, CD62L, CXCR5); cytokine-receptors (IL-15Ra) (FIG. 12). Thus, in addition to lymph node homing markers, they also expressed markers typical for gut cells (CD161). When compared to AGM, the HLA-E restricted CD8 T from SIV-infected macaques expressed no or very low levels of CXCR5 (not shown). As CXCR5 directs B and T lymphocytes into B-cell follicles of lymphoid tissues (Crotty, 2014; Cyster et al., 2000), this result is of major importance as it indicates that HLA-E restricted CD8 T cells of AGM can migrate into the site of the major viral reservoir (Brenchley et al., 2012; Lindqvist et al., 2012; Petrovas et al., 2012).

The cells shared some characteristics with other HLA-E restricted CD8 T cells (Joosten et al., 2016), but it is not clear if they are the same. In order to characterize them more deeply, we performed a whole genome transcriptome analysis in order to determine the whole range of genes expressed in these cells as compared to other more classical CD8 T cells by RNAseq in 4 animals (FIG. 3). High stringency criteria were applied in the statistical analysis of the genomic data. The RNAseq analysis revealed that HLA-E restricted CD8 T cells, which are expanded in AGM, express indeed many NK cell markers (KIR2DL4, KIR3DL4, KIR3DL7, NKG2A/C, NKG7 . . . ) as well as additional homing receptors, such as CXCR6, and cytokine receptors, such as IL12R, IL23R. Of note, they also expressed cytolytic granules, such as Granzyme A and B and Perforin, and thus seem constantly ready to kill. Indeed, the molecular profiles indicate that these cells are in a specific metabolic state (LAMTOR1, CD73) where they might be less dependent on energy for their effector function.

Figure 2C:
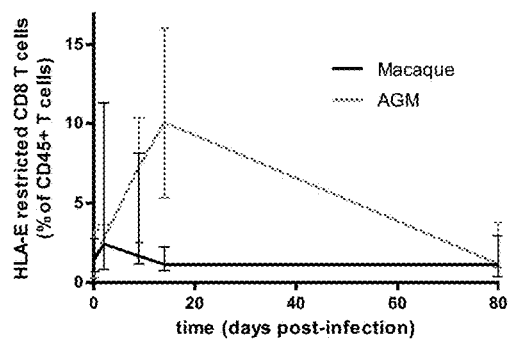

HLA-E Restricted CD8 T Cells are Induced Early on in Tissues During Non Pathogenic SIV Infection In order to address the roles and relative contributions of HLA-E restricted CD8 T cells in pathogenic and non-pathogenic SIV infections, we followed these cells in a very close kinetics in the blood, lymph nodes and rectal biopsies of AGM and macaque. In AGM blood, we observed a transient depletion of these cells during the early acute phase of infection followed by an increase that peaks at the viral set point (35 days post-infection) (FIG. 2A). The increase was even more striking in the gut where they represented up to 10% of the lymphoid cells at day 9 post-infection (FIG. 2C), leading to the hypothesis that the depletion observed early in the blood is due to a relocalization of these cells. In macaque, very low levels of HLA-E restricted CD8 T cells were detected in blood and tissues during the whole course of SIV infection (FIG. 2C).

Figure 4A:
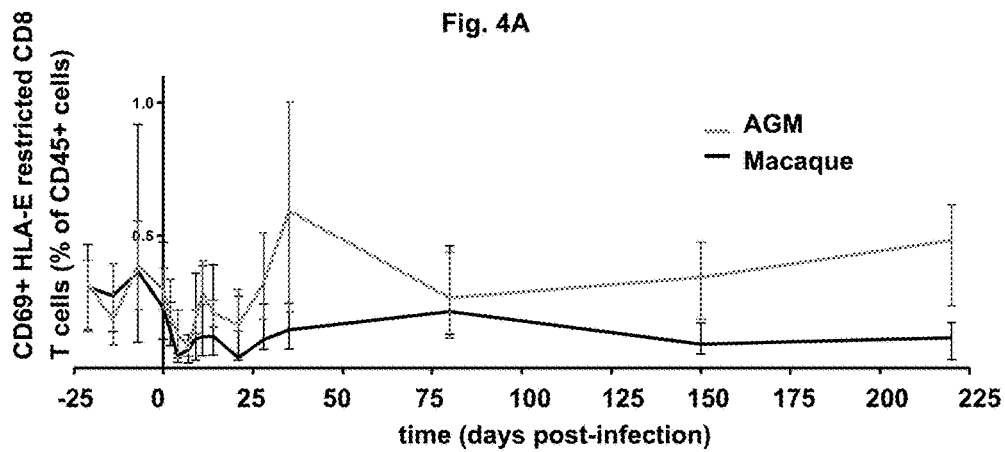
FIG. 4A-C: Follow-up of activated (% CD69+)(FIG. 4A), cytolytic and functional (% Perforin+(FIG. 4B), CD107a levels (FIG. 4C)) MHC-E restricted CD8 T cells during SIV infection in the blood of 6 AGM and 6 macaques by flow cytometry. Data are presented as medians and interquartile ranges.
Figure 4B:
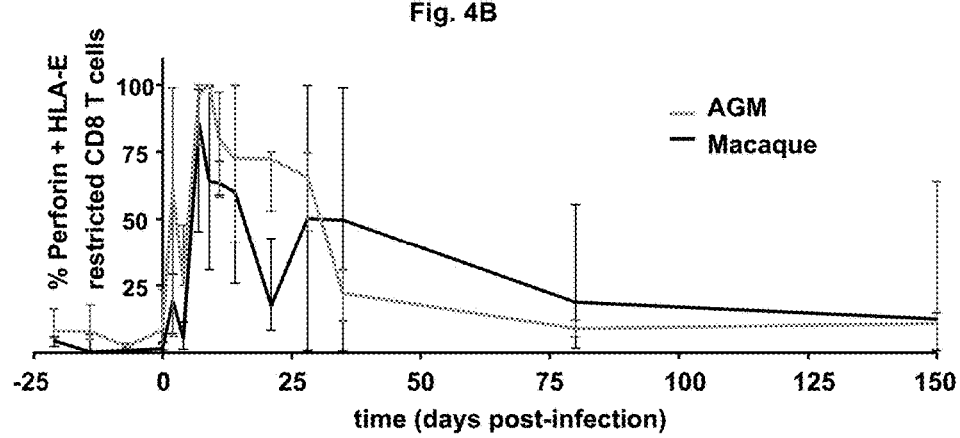
Figure 4C:
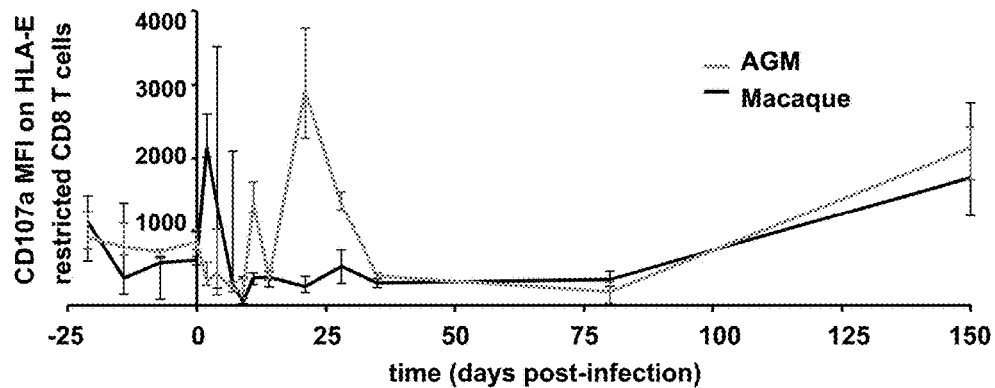

The HLA-E restricted CD8 T cells expressed more often CD69 in non-pathogenic infection (FIG. 4A). They showed an effector phenotype as measured by the presence of cytolytic molecules in vivo (CD107a, Perforin) (FIGS. 4B and C), further supporting a potential strong cytolytic activity in situ.

Figure 5:
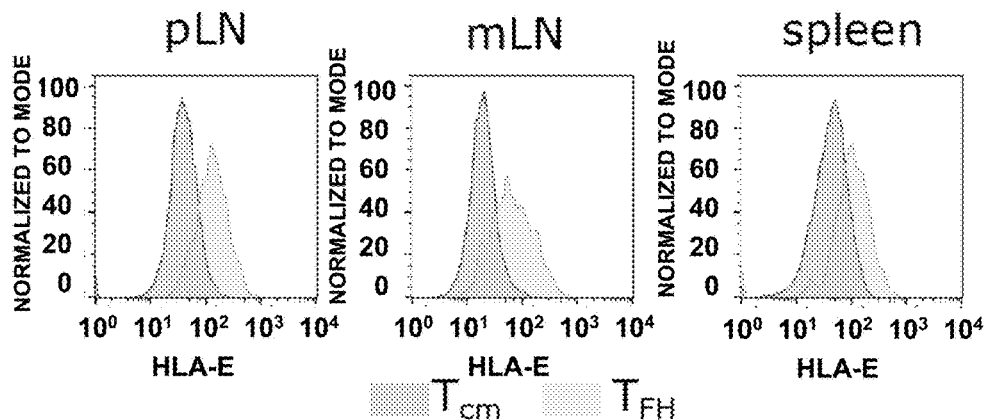
FIG. 5: MHC-E positive CD4 T cells in AGM and macaques in tissues. $T_{FH}$ express very high levels of MHC-E. pLN=peripheral lymph nodes; mLN=mesenteric (intestinal) lymph nodes.

The Preferential Target Cells of HIV/SIV Express Highest Levels of HLA-E in the Animal Models of HIV We quantified HLA-E expression on target cells for HIV and SIV, i.e. CD4 T cells. Similar to what has been reported in humans, HLA-E was strongly expressed on $T_{FH}$ cells in the monkeys (FIG. 5). Of note, the levels were higher than on any other CD4 T cells evaluated and higher than on $T_{CM}$. This indicates that in particular $T_{FH}$ cells can potentially be recognized and killed by MHC-E restricted CD8 T and NK cells.

HSP60 Gene Expression Persists Only in Macaque CD4 Cells

Figure 6A:
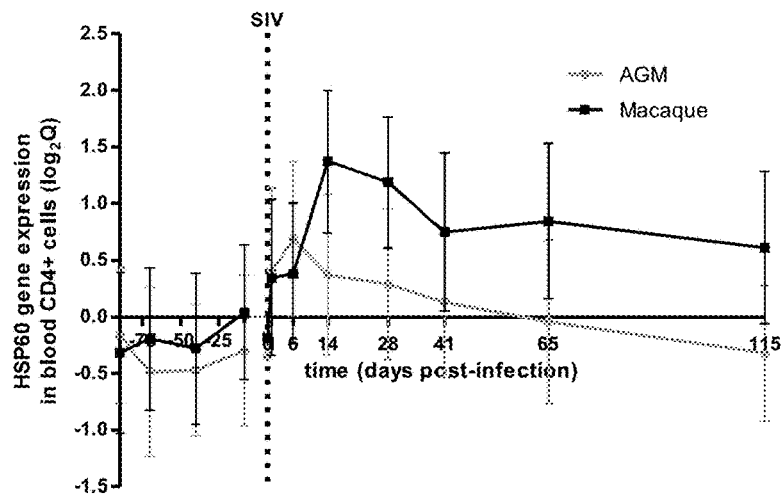
FIG. 6A-B: Microarray gene expression profiles of HSP60 in CD4+ cells from blood (FIG. 6A) and peripheral lymph nodes (FIG. 6B) in 6 AGM and 6 macaques. Mean values of the $\log_2$ Q (foldchange) and the standard deviations are represented (data from Jacquelin B et al., *J Clin Invest*, 2009).
Figure 6B:
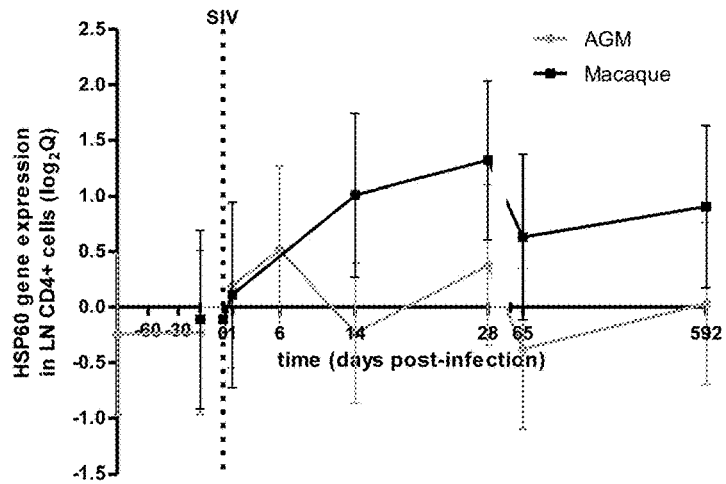

While HIV infection induces increases of HLA-E expression through binding of viral peptides to HLA-E in vitro, it is also possible that in vivo, HLA-E binds the stress protein HSP60 in the target cells of HIV that might be stressed by the infection (Anraku et al., 2012; Wallin et al., 2002). It has been shown that HIV-infected cells indeed produce HSP60 (Bartz et al., 1994). We previously measured HSP60 gene expression in blood and lymph node CD4 cells of AGM and macaques with the microarray technology (Jacquelin et al., 2009). HSP60 is immediately upregulated in response to SIV infection in both AGM and macaque, although at lower levels in AGM (FIG. 6). From day 6-14 post-infection, HSP60 gene expression became progressively weaker in AGM and returned to baseline levels, while it remained sustained in macaque. Similar profiles were observed in blood and lymph nodes. Infected cells in pathogenic infection might thus present more often HSP60 instead of other peptides through HLA-E than in non-pathogenic infection and be recognized differentially by HLA-E restricted CD8 T and NK cells during pathogenic and non-pathogenic infection. In addition, HLA-E restricted CD8 T and NK cells are present to only low levels in pathogenic infection.

Figure 7A:
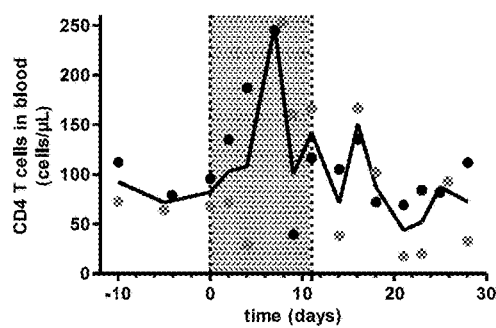
FIG. 7A-D: CD4 T cell (FIG. 7A), classical CD8 T cell (FIG. 7B) and MHC-E restricted CD8 T cell counts (FIG. 7C) in the blood of two SIV-infected macaques upon GA treatment. Follow-up of the percentage of CD4 T cells expressing MHC-E on their surface (FIG. 7D). In each graph, each animal is represented in a different color, which is the same through all the graphs; the bold lines represent the median from the 2 animals and the grey area indicates the period of GA treatment.

GA Treatment of Chronically SIV Infected Macaques Induces a Transient Increase of HLA-E Restricted CD8 T Cells and CD4 T Cells in Blood We aimed to test that if we can induce HLA-E restricted lymphocytes in HIV/SIV pathogenic infection and whether this has an impact on the control of the viral reservoirs. In a pilot study, we treated two chronically SIVmac-infected macaques for a short time period with GA. Based on the data of pharmacokinetic and pharmacodynamics studies of the drug in monkeys (Ramot et al., 2011b; TEITELBAUM et al., 2004), we injected 18 mg of GA three times per week for 2 weeks to the 2 macaques infected with SIV for 2 years. The two macaques were in an advanced stage of infection (<200 CD4 T cells/mm$^3$) (FIG. 7A). We sampled the two animals every 2 to 7 days during and after the GA treatment for two months and sacrificed them to study the tissues.

Figure 7B:
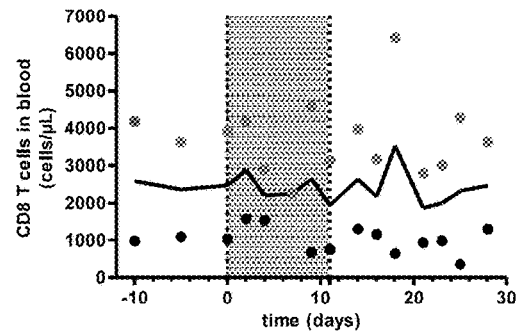
Figure 7C:
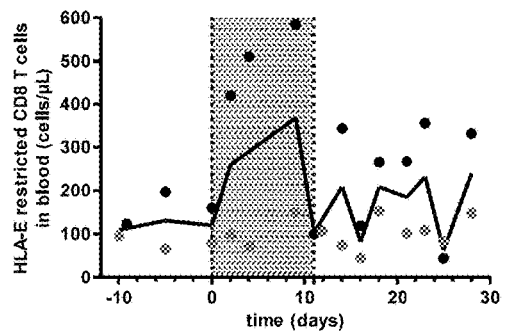

Administration of GA lead to an increase of HLA-E restricted CD8 T cell counts (FIG. 7C), while no major effect was observed on the classical CD8 T cell population (FIG. 7B).

Figure 8A:
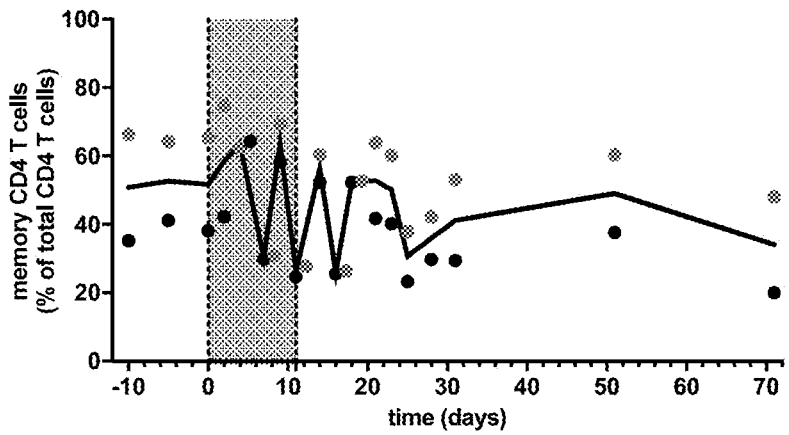
FIG. 8A-C: Follow-up of total memory CD4 T cell (FIG. 8A), $T_{CM}$ (FIG. 8B), and $T_{TM}$ (FIG. 8C) in the blood of two SIV-infected macaques upon GA treatment. In each graph, each animal is represented in a different color, which is the same through all the graphs; the bold lines represent the median from the 2 animals and the grey area indicates the period of GA treatment.
Figure 8B:
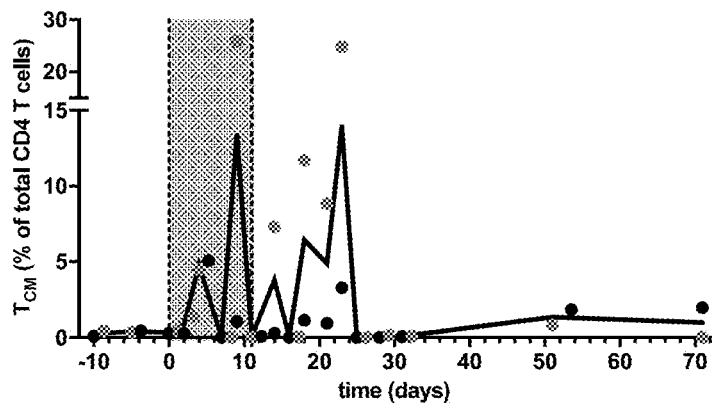
Figure 8C:
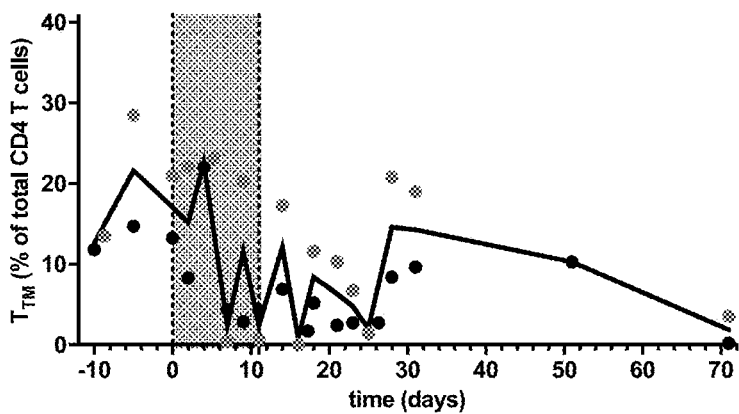

GA injection also lead to an increase of the CD4 T cells during the time of treatment (FIG. 7A). Modulations of the memory CD4 T cell subsets were observed until 3 weeks after treatment cessation. $T_{CM}$ increased transiently while Tim were persistently diminished (FIG. 8).

Figure 7D:
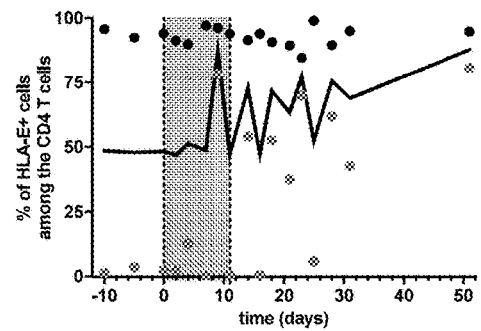

We looked at the expression of HLA-E on CD4 T cells. It was already very high in one animal before treatment and remained as high (FIG. 7D). The animal the most advanced in disease didn't express HLA-E before the treatment and was able to increase HLA-E levels on the surface of the CD4 T cells upon GA treatment and the levels continued to increase in this animal even after treatment cessation.

The GA Treatment Induces a Decrease of the Viral Load that Persists Over Time

Figure 9A:
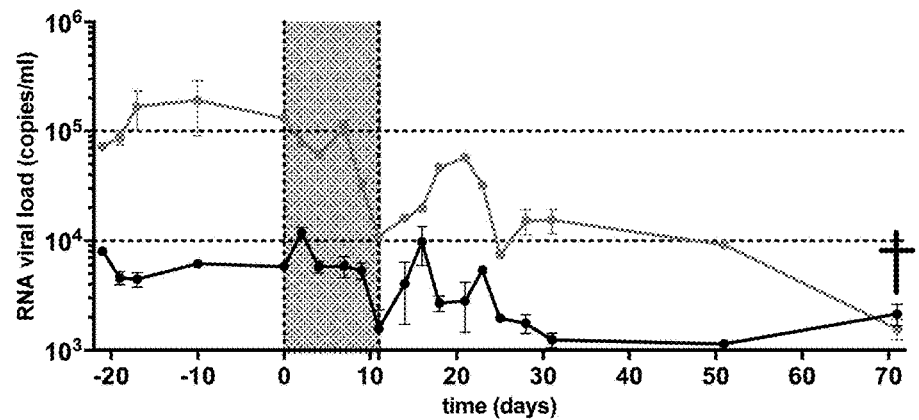
FIG. 9A-C: Plasma viral RNA copy numbers were measured by real-time PCR in the 2 macaques infected with SIVmac251 and treated with GA. The viral load was quantified as previously described (Jacquelin et al, 2009; Huot et al, 2017).
Figure 9B:
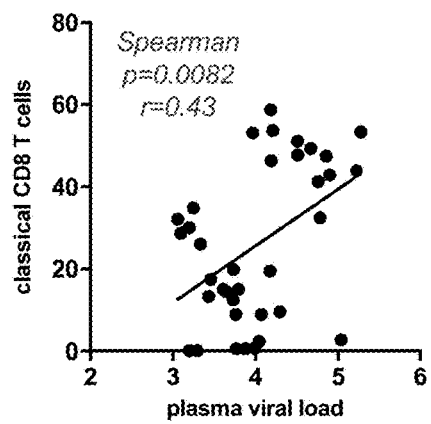
Figure 9C:
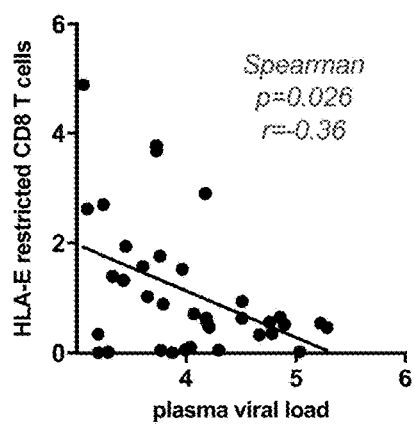

The most striking impact of the GA treatment was on the viral load (FIG. 9). During the treatment, a one log decrease of the viral load in the blood was observed. Even more stoning was the fact that this decrease persists after stopping the treatment reaching almost a 2 logs decrease in one animal. This is a major result as compared to cART as stopping cART leads to a rapid rebound of the viral load (Harrigan et al., 1999).

Moreover, this decrease was positively correlated to the classical CD8 T cells and inversely correlated to the HLA-E restricted CD8 T cells (FIG. 9), supporting the hypothesis that HLA-E restricted CD8 T cells might be the cells playing a role in the control of the virus under GA treatment and not other cytotoxic CD8 T cells.

Figure 10A:
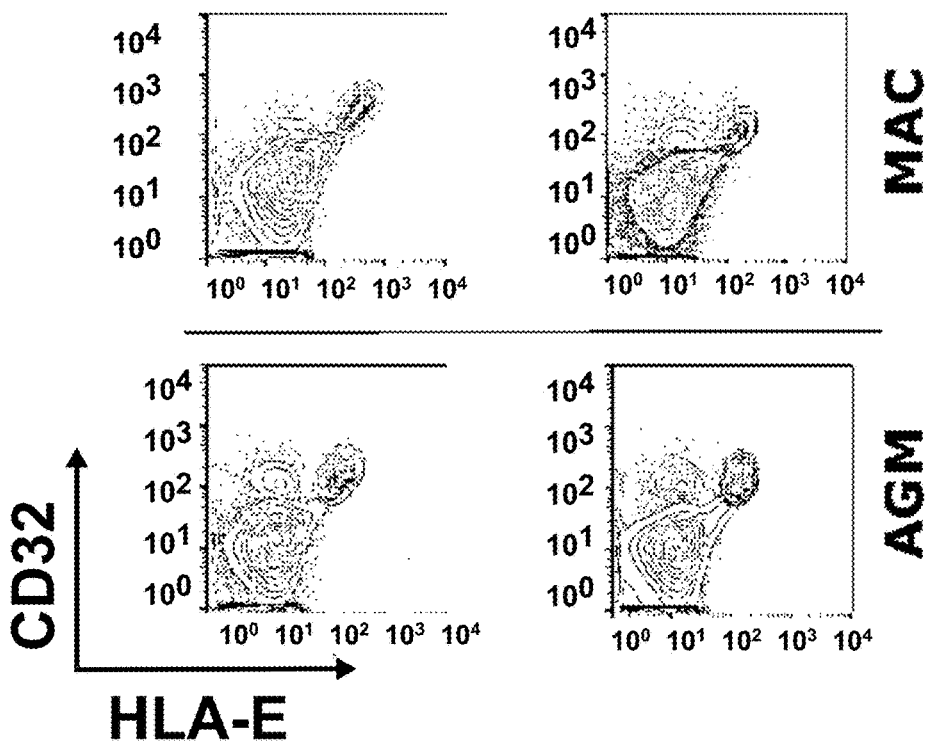
FIG. 10A-B: Frequencies of $CD32a^{high}CD4$ T cells expressing MHC-E before and after GA treatment. CD32a has been recently described as to be the best marker of latently HIV-infected cells (Descours et al., 2017).
Figure 10B:
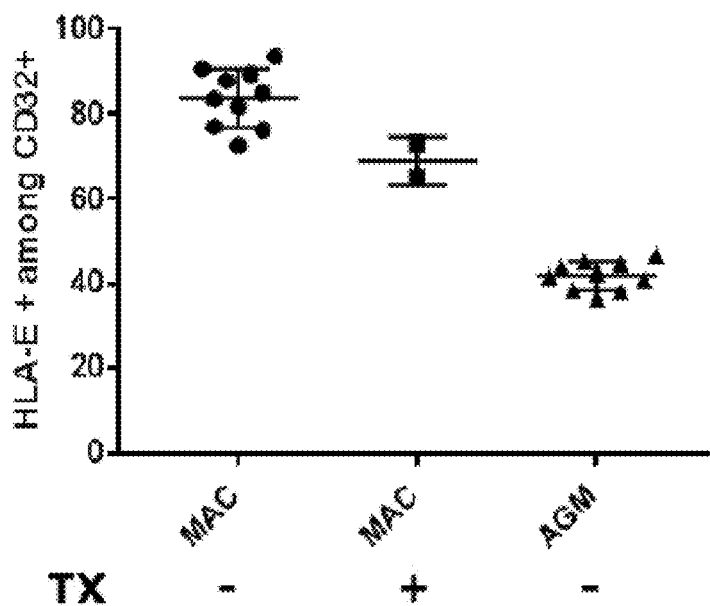

We also quantified the pool of latently infected cells using the markers recently described (Descours et al., 2017). The results show that most latently infected cells (CD32a$^{high}$ CD4 T) express HLA-E (80% in macaques) and that GA treatment targets CD32a$^{high}$ CD4 T cells expressing HLA-E, suggesting that the treatment preferentially induced depletion of the HLA-E expressing cells, in line with our hypothesis (FIG. 10).

Decrease of Memory CD4 T Cells in Tissues after GA Treatment

Figure 11A:
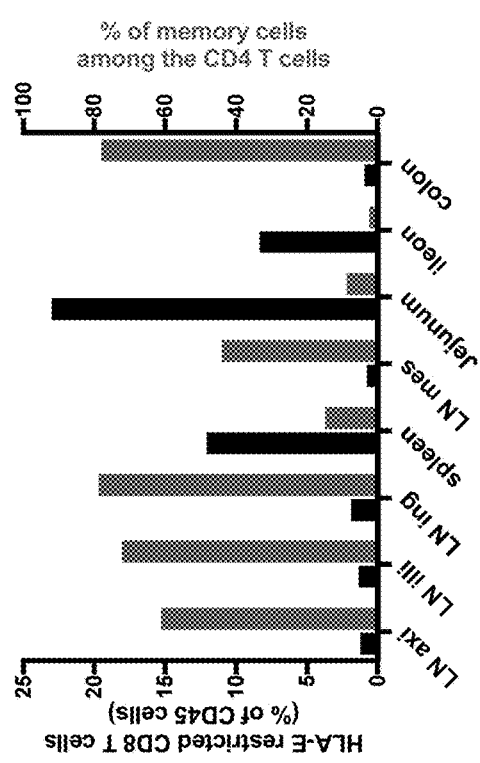
FIG. 11A-B.
Figure 11B:
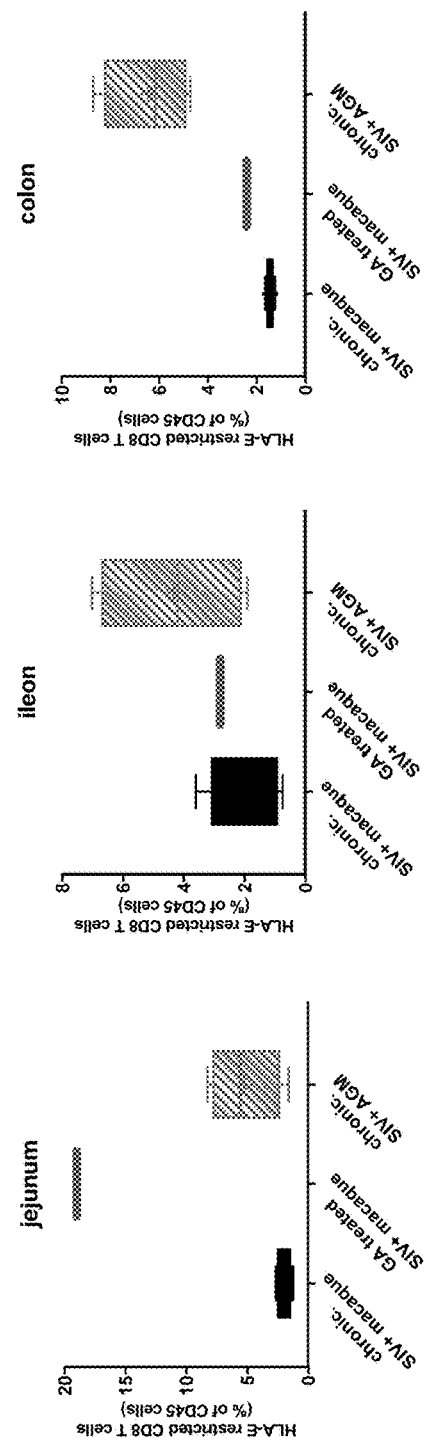

The study of the tissues at euthanasia showed that sites with the highest percentages of HLA-E restricted CD8 T cells were the spleen and the small intestine (ileon and jejunum) (FIG. 11). Interestingly, these were the same sites that displayed particular low percentages of HIV target cells (memory CD4 T cells). This result comforts in the idea that HLA-E restricted CD8 T cells are able to target infected cells in tissues. Moreover, in the GA treated animal, the levels of HLA-E restricted CD8 T cells in the intestine reached comparable levels or even higher to those in AGM (FIG. 11). Thus, the control of the reservoir cells in the small intestine might be a first step towards protection against AIDS. The control of the virus in the gut is indeed key to the pathogenesis as this tissue harbors 83-95% of all HIV infected cells in the body and that some of its parts, such as the ileum, might be a site of ongoing replication in patients on cART (Wong and Yukl, 2016).

Increase of Cytotoxic Activity of HLA-E Restricted CD8 T Cells and NK Cells after GA Treatment GA induces an increase of not only the cytotoxic activity of HLA-E restricted CD8 T cells but also the cytotoxic activity of HLA-E restricted (NKG2A/C+) NK cells during and up to 50 days after the treatment as shown by the frequency of CD107a (FIG. 13). In addition, the sharp increase of the cytotoxic activity of HLA-E restricted CD8 T cells and NK cells at around day 25 (60% of CD107a versus 20%—FIGS. 13C and 13D) in the GA treated macaques correlates with a sharp decrease of SIV viral load starting at around day +25 as shown in FIG. 9A.

REFERENCES

Allers, K.; Hutter, G.; Hofmann, J.; Loddenkemper, C.; Rieger, K.; Thiel, E.; Schneider, T. (2011). "Evidence for the cure of HIV infection by CCR5 32/32 stem cell transplantation". Blood. 117 (10): 2791-2799.

Anraku, I., Rajasuriar, R., Dobbin, C., Brown, R., Lewin, S. R., and Suhrbier, A. (2012). Circulating Heat Shock Protein 60 Levels Are Elevated in HIV Patients and Are Reduced by Anti-Retroviral Therapy. PLOS ONE 7, e45291.

Arlettaz, L., Villard, J., de Rham, C., Degermann, S., Chapuis, B., Huard, B., and Roosnek, E. (2004). Activating CD94:NKG2C and inhibitory CD94:NKG2A receptors are expressed by distinct subsets of committed CD8+ TCR αβ lymphocytes. Eur. J. Immunol. 34, 3456-3464.

Banga, R., Procopio, F. A., Noto, A., Pollakis, G., Cavassini, M., Ohmiti, K., Corpataux, J.-M., de Leval, L., Pantaleo, G., and Perreau, M. (2016). PD-1+ and follicular helper T cells are responsible for persistent HIV-1 transcription in treated aviremic individuals. Nat Med 22, 754-761.

Bartz, S. R., Pauza, C. D., Ivanyi, J., Jindal, S., Welch, W. J., and Malkovsky, M. (1994). An Hsp60 related protein is associated with purified HIV and SIV. J. Med. Primatol. 23, 151-154.

Brenchley, J. M., Vinton, C., Tabb, B., Hao, X. P., Connick, E., Paiardini, M., Lifson, J. D., Silvestri, G., and Estes, J. D. (2012). Differential infection patterns of CD4+ T cells and lymphoid tissue viral burden distinguish progressive and nonprogressive lentiviral infections. Blood 120, 4172-4181.

Brochet B. Long term effects of glatiramer acetate in multiple sclerosis. Rev Neurol (Paris). 2008 November; 164 (11):917-26. doi: 10.1016/j.neurol.2008.02.045.

Buranapraditkun, S., Pissani, F., Teigler, J. E., Schultz, B. T., Alter, G., Marovich, M., Robb, M. L., Eller, M. A., Martin, J., Deeks, S., et al. (2017). Preservation of peripheral T follicular helper cell function in HIV controllers. J. Virol. 2017. pii: JVI.00497-17. doi: 10.1128/JVI.00497-17.

Calin, R., Hamimi, C., Lambert-Niclot, S., Carcelain, G., Bellet, J., Assoumou, L., Tubiana, R., Calvez, V., Dudoit, Y., Costagliola, D., et al. (2016). Treatment interruption in chronically HIV-infected patients with an ultralow HIV reservoir. AIDS 30.

Cartwright, E. K., McGary, C. S., Cervasi, B., Micci, L., Lawson, B., Elliott, S. T. C., Collman, R. G., Bosinger, S. E., Paiardini, M., Vanderford, T. H., et al. (2014). Divergent CD4+ T Memory Stem Cell Dynamics in Pathogenic and Nonpathogenic Simian Immunodeficiency Virus Infections. J. Immunol. 192, 4666.

Chahroudi, A., Bosinger, S. E., Vanderford, T. H., Paiardini, M., and Silvestri, G. (2012). Natural SIV hosts: showing AIDS the door. Science 335, 1188-1193.

Chomont, N., El-Far, M., Ancuta, P., Trautmann, L., Procopio, F. A., Yassine-Diab, B., Boucher, G., Boulassel, M.-R., Ghattas, G., Brenchley, J. M., et al. (2009). HIV reservoir size and persistence are driven by T cell survival and homeostatic proliferation. Nat Med 15, 893-900.

Chun, T.-W., Moir, S., and Fauci, A. S. (2015). HIV reservoirs as obstacles and opportunities for an HIV cure. Nat Immunol 16, 584-589.

Crotty, S. (2014). T Follicular Helper Cell Differentiation, Function, and Roles in Disease. Immunity 41, 529-542.

Davey, R. T., Bhat, N., Yoder, C., Chun, T.-W., Metcalf, J. A., Dewar, R., Natarajan, V., Lempicki, R. A., Adelsberger, J. W., Miller, K. D., et al. (1999). HIV-1 and T cell dynamics after interruption of highly active antiretroviral therapy (HAART) in patients with a history of sustained viral suppression. Proc. Natl. Acad. Sci. 96, 15109-15114.

Descours, B., Avettand-Fenoel, V., Blanc, C., Samri, A., Melard, A., Supervie, V., Theodorou, I., Carcelain, G., Rouzioux, C., and Autran, B. (2012). Immune responses driven by protective human leukocyte antigen alleles from long-term nonprogressors are associated with low HIV reservoir in central memory CD4 T cells. Clin Infect Dis 54, 1495-1503.

Descours B, Petitjean G, Lopez-Zaragoza J L, Bruel T, Raffel R, Psomas C, Reynes J, Lacabaratz C, Levy Y, Schwartz O, Lelievre J D, Benkirane M. CD32A is a marker of a CD4 T-cel HIV reservoir harbouring replication-competent proviruses. Nature. 2017 Mar. 23; 543 (7646):564-567. doi: 10.1038/nature21710. Epub 2017 Mar. 15.

Devaraj, S., Dasu, M. R., Park, S. H., and halal, I. (2009). Increased levels of ligands of Toll-like receptors 2 and 4 in type 1 diabetes. Diabetologia 52, 1665-1668.

Fukazawa, Y., Lum, R., Okoye, A. A., Park, H., Matsuda, K., Bae, J. Y., Hagen, S. I., Shoemaker, R., Deleage, C., Lucero, C., et al. (2015). B cell follicle sanctuary permits persistent productive simian immunodeficiency virus infection in elite controllers. Nat Med 21, 132-139.

Garcia-Tellez, T., Huot, N., Ploquin, M. J., Rascle, P., Jacquelin, B., and Müller-Trutwin, M. (2016). Non-human primates in HIV research: Achievements, limits and alternatives. Infect. Genet. Evol. 46, 324-332.

Gong, F., Song, S., Lv, G., Pan, Y., Zhang, D., and Jiang, H. (2012). Human leukocyte antigen E in human cytomegalovirus infection: friend or foe? Acta Biochim. Biophys. Sin. 44, 551-554.

Gueye, A., Diop, O. M., Ploquin, M. J. Y., Kornfeld, C., Faye, A., Cumont, M.-C., Hurtrel, B., Barré-Sinoussi, F., and Müller-Trutwin, M. C. (2004). Viral load in tissues during the early and chronic phase of non-pathogenic SIVagm infection. J. Med. Primatol. 33, 83-97.

Hansen, S. G., Wu, H. L., Burwitz, B. J., Hughes, C. M., Hammond, K. B., Ventura, A. B., Reed, J. S., Gilbride, R. M., Ainslie, E., Morrow, D. W., et al. (2016). Broadly targeted CD8+ T cell responses restricted by major histocompatibility complex E. Science 351, 714.

He, R., Hou, S., Liu, C., Zhang, A., Bai, Q., Han, M., Yang, Y., Wei, G., Shen, T., Yang, X., et al. (2016). Follicular CXCR5-expressing CD8(+) T cells curtail chronic viral infection. NATURE 537, 412+.

Huot N, Jacquelin B, Garcia-Tellez T, Rascle P, Ploquin M, Madec Y, Reeves R K, Derreudre-Bosquet N & Müller-Trutwin M. NK cells migrate into and control SIV replication in lymph node follicles in African green monkeys. Nat Med. 2017 November; 23(11):1277-1286.

Hutter, G., Nowak, D., Mossner, M., Ganepola, S., Mussig, A., Allers, K., Schneider, T., Hofmann, J., Kucherer, C., Blau, O., et al. 2009 Long-term control of HIV by CCR5 Delta32/Delta32 stem-cell transplantation. N Engl J Med 360, 692-698.

Jacquelin, B., Mayau, V., Targat, B., Liovat, A. S., Kunkel, D., Petitjean, G., Dillies, M. A., Rogues, P., Butor, C., Silvestri, G., et al. (2009). Nonpathogenic SIV infection of African green monkeys induces a strong but rapidly controlled type I IFN response. J Clin Invest 119, 3544-3555.

Jacquelin B., G. Petitjean, D. Kunkel, A-S. Liovat, S. P. Jochems, K. A. Rogers, M. J. Ploquin, F. Barré-Sinoussi, N. Dereuddre-Bosquet, P. Lebon, R. Le Grand, F. Villinger & M. Müller-Trutwin. Innate Immune Responses and Rapid Control of Inflammation in African Green Monkeys Treated or not with Interferon-Alpha during Primary SIVagm Infection. PLoS Pathog. 2014 Jul. 3; 10(7):e10042412014.

Jason G. Cyster, K. Mark Ansel, Karin Reif, Eric H. Ekland, Paul L. Hyman, H. Lucy Tang, Sanjiv A. Luther, and Vu N. Ngo (2000). Follicular stromal cells and lymphocyte homing to follicles. Immunol. Rev. 176, 181-193.

Jiang, H., Canfield, S. M., Gallagher, M. P., Jiang, H. H., Jiang, Y., Zheng, Z., and Chess, L. (2010). HLA-E-restricted regulatory CD8+ T cells are involved in development and control of human autoimmune type 1 diabetes. J. Clin. Invest. 120, 3641-3650.

Joosten, S. A., Sullivan, L. C., and Ottenhoff, T. H. M. (2016). Characteristics of HLA-E Restricted T-Cell Responses and Their Role in Infectious Diseases. J. Immunol. Res.

Kim, H.-J., Verbinnen, B., Tang, X., Lu, L., and Cantor, H. (2010). Inhibition of follicular T-helper cells by CD8(+) regulatory T cells is essential for self tolerance. NATURE 467, 328-U107.

Kim, H.-J., Wang, X., Radfar, S., Sproule, T. J., Roopenian, D. C., and Cantor, H. (2011). CD8+ T regulatory cells express the Ly49 Class I MHC receptor and are defective in autoimmune prone B6-Yaa mice. Proc. Natl. Acad. Sci. 108, 2010-2015.

Lee, N., Goodlett, D. R., Ishitani, A., Marquardt, H., and Geraghty, D. E. (1998). HLA-E Surface Expression Depends on Binding of TAP-Dependent Peptides Derived from Certain HLA Class I Signal Sequences. J. Immunol. 160, 4951.

Leong, Y. A., Chen, Y., Ong, H. S., Wu, D., Man, K., Deleage, C., Minnich, M., Meckiff, B. J., Wei, Y., Hou, Z., et al. (2016). CXCR5(+) follicular cytotoxic T cells control viral infection in B cell follicles. Nat. Immunol. 17, 1187+.

Lindqvist, M., van Lunzen, J., Soghoian, D. Z., Kuhl, B. D., Ranasinghe, S., Kranias, G., Flanders, M. D., Cutler, S., Yudanin, N., Muller, M. I., et al. (2012). Expansion of HIV-specific T follicular helper cells in chronic HIV infection. J Clin Invest 122, 3271-3280.

Long, X., Cheng, Q., Liang, H., Zhao, J., Wang, J., Wang, W., Tomlinson, S., Chen, L., Atkinson, C., Zhang, B., et al. (2017). Memory CD4(+) T cells are suppressed by CD8(+) regulatory T cells in vitro and in vivo. Am. J. Transl. Res. 9, 63-78.

Lorenzo-Redondo, R., Fryer, H. R., Bedford, T., Kim, E.-Y., Archer, J., Pond, S. L. K., Chung, Y.-S., Penugonda, S., Chipman, J., Fletcher, C. V., et al. (2016). Persistent HIV-1 replication maintains the tissue reservoir during therapy. Nature 530, 51-56.

Lu, L., and Cantor, H. (2008). Generation and Regulation of CD8+Regulatory T Cells. Cell Mol Immunol 5, 401-406.

Massanella, M., Fromentin, R., and Chomont, N. (2016). Residual inflammation and viral reservoirs: Alliance against an HIV cure. Curr Opin HIV AIDS 11, 234-241.

Michaëlsson, J., Teixeira de Matos, C., Achour, A., Lanier, L. L., Kärre, K., and Söderström, K. (2002). A Signal Peptide Derived from hsp60 Binds HLA-E and Interferes with CD94/NKG2A Recognition. J. Exp. Med. 196, 1403.

Miles, B., and Connick, E. (2016a). TFH in HIV Latency and as Sources of Replication-Competent Virus. Spec. Issue Microb. Endur. 24, 338-344.

Miles, B., Miller, S. M., Folkvord, J. M., Levy, D. N., Rakasz, E. G., Skinner, P. J., and Connick, E. (2016b). Follicular Regulatory CD8 T Cells Impair the Germinal Center Response in SIV and Ex Vivo HIV Infection. PLOS Pathog. 12, e1005924.

Moukambi, F., Rodrigues, V., Fortier, Y., Rabezanahary, H., Borde, C., Krust, B., Andreani, G., Silvestre, R., Petrovas, C., Laforge, M., et al. (2017). CD4 T Follicular Helper Cells and HIV Infection: Friends or Enemies? Front. Immunol. 8, 135.

Nattermann, J., Nischalke, H., Hofmeister, V., Kupfer, B., Ahlenstiel, G., Feldmann, G., Rockstroh, J., Weiss, E., Sauerbruch, T., and Spengler, U. (2005). HIV-1 infection leads to increased HLA-E expression resulting in impaired function of natural killer cells. Antivir. Ther. 10, 95-107.

Paiardini, M., Cervasi, B., Reyes-Aviles, E., Micci, L., Ortiz, A. M., Chahroudi, A., Vinton, C., Gordon, S. N., Bosinger, S. E., Francella, N., et al. (2011). Low levels of SIV infection in sooty mangabey central memory CD(4) (+) T cells are associated with limited CCR5 expression. Nat. Med. 17, 830-836.

Petrovas, C., Yamamoto, T., Gerner, M. Y., Boswell, K. L., Wloka, K., Smith, E. C., Ambrozak, D. R., Sandler, N. G., Timmer, K. J., Sun, X., et al. (2012). CD4 T follicular helper cell dynamics during SIV infection. J Clin Invest 122, 3281-3294.

Ploquin, M. J., Silvestri, G., and Müller-Trutwin, M. (2016). Immune activation in HIV infection: what can the natural hosts of simian immunodeficiency virus teach us? Curr. Opin. HIV AIDS 11.

Ramot, Y., Rosenstock, M., Klinger, E., Bursztyn, D., Nyska, A., and Shinar, D. M. (2011a). Comparative Long-Term Preclinical Safety Evaluation of Two Glatiramoid Compounds (Glatiramer Acetate, Copaxone®, and TV-5010, Protiramer) in Rats and Monkeys. Toxicol. Pathol. 40, 40-54.

Saez-Cirion, A., Bacchus, C., Hocqueloux, L., Avettand-Fenoel, V., Girault, I., Lecuroux, C., Potard, V., Versmisse, P., Melard, A., Prazuck, T., et al. (2013). Post-treatment HIV-1 controllers with a long-term virological remission after the interruption of early initiated antiretroviral therapy ANRS VISCONTI Study. PLoS Pathog 9, e1003211.

Saez-Cirion, A., Jacquelin, B., Barre-Sinoussi, F., and Muller-Trutwin, M. (2014). Immune responses during spontaneous control of HIV and AIDS: what is the hope for a cure? Philos Trans R Soc Lond B Biol Sci 369, 20130436.

Shamaei-Tousi, A., Stephens, J. W., Bin, R., Cooper, J. A., Steptoe, A., Coates, A. R. M., Henderson, B., and Humphries, S. E. (2006). Association between plasma levels of heat shock protein 60 and cardiovascular disease in patients with diabetes mellitus. Eur. Heart J. 27, 1565-1570.

Sinha, S., Itani, F. R., and Karandikar, N.J. (2014). Immune regulation of multiple sclerosis by CD8+ T cells. Immunol. Res. 59, 254-265.

Sinha, S., Boyden, A. W., Itani, F. R., Crawford, M. P., and Karandikar, N.J. (2015). CD8+ T-Cells as Immune Regulators of Multiple Sclerosis. Front. Immunol. 6, 619.

TEITELBAUM, D., AHARONI, R., KLINGER, E., KREITMAN, R., RAYMOND, E., MALLEY, A., SHOFTI, R., SELA, M., and ARNON, R. (2004). Oral Glatiramer Acetate in Experimental Autoimmune Encephalomyelitis: Clinical and Immunological Studies. Ann. N. Y. Acad. Sci. 1029, 239-249.

Tennakoon, D. K., Mehta, R. S., Ortega, S. B., Bhoj, V., Racke, M. K., and Karandikar, N.J. (2006). Therapeutic Induction of Regulatory, Cytotoxic CD8+ T Cells in Multiple Sclerosis. J. Immunol. 176, 7119.

Trono, D., Van Lint, C., Rouzioux, C., Verdin, E., Barré-Sinoussi, F., Chun, T.-W., and Chomont, N. (2010). HIV Persistence and the Prospect of Long-Term Drug-Free Remissions for HIV-Infected Individuals. Science 329, 174.

Wallin, R. P., Lundqvist, A., More, S. H., von Bonin, A., Kiessling, R., and Ljunggren, H.-G. (2002). Heat-shock proteins as activators of the innate immune system. Trends Immunol. 23, 130-135.

Wong, J. K., and Yukl, S. A. (2016). Tissue reservoirs of HIV. Curr Opin HIV AIDS 11, 362-370.

Yao, Y., Han, W., Liang, J., Ji, J., Wang, J., Cantor, H., and Lu, L. (2013). Glatiramer acetate ameliorates inflammatory bowel disease in mice through the induction of Qa-1-restricted CD8+ regulatory cells. Eur. J. Immunol. 43, 125-136.

The invention claimed is:

1. A method for detecting the presence or absence of HIV-1-specific nucleic acid comprising:
   a) administering a dose of glatiramer acetate to an HIV-1-infected patient,
   wherein the HIV-infected patient has never been diagnosed with HIV encephalopathy;
   b) taking a blood sample from the patient;
   c) preparing RNA from the blood sample;
   d) preparing cDNA from the RNA;
   e) amplifying the cDNA by making DNA or RNA copies thereof to generate an amplified sample; and
   f) detecting the presence or absence of HIV-1-specific nucleic acid in the amplified sample.

2. The method of claim 1, wherein the method is repeated at least twice.

3. The method of claim 1, wherein the method comprises making DNA copies of HIV-1 cDNA with a polymerase chain reaction (PCR).

4. The method of claim 3, wherein the PCR is a real-time RT-PCR.

5. The method of claim 1, wherein the method comprises making RNA copies of HIV-1 cDNA with T7 polymerase.

6. The method of claim 1, wherein the method comprises detecting the presence or absence of HIV-1-specific nucleic acid in the amplified sample with a fluorescent label.

7. The method of claim 1, wherein the HIV-1-infected patient has been treated with an anti-HIV inhibitor within 1 month prior to or after being administered at least one dose of glatiramer acetate.

8. The method of claim 1, wherein cells in the blood sample are removed to generate a plasma sample and RNA is prepared from the plasma sample.

9. The method of claim 8, wherein the plasma sample is subjected to ultracentrifugation prior to preparing RNA.

10. The method of claim 1, wherein, the cDNA is prepared using an HIV-1-specific primer and a reverse transcriptase.

11. A method for detecting the presence or absence of HIV-1-specific nucleic acid comprising:
    a) providing a blood sample from an HIV-1-infected patient treated with at least one dose of glatiramer acetate,
    wherein the HIV-infected patient has never been diagnosed with HIV encephalopathy;
    b) preparing RNA from the blood sample;
    c) preparing cDNA from the RNA;
    d) amplifying the cDNA by making DNA or RNA copies thereof to generate an amplified sample; and
    e) detecting the presence or absence of HIV-1-specific nucleic acid in the amplified sample.

12. The method of claim 11, wherein the method is repeated at least twice.

13. The method of claim 11, wherein the method comprises making DNA copies of HIV-1 cDNA with a polymerase chain reaction (PCR).

14. The method of claim 13, wherein the PCR is a real-time RT-PCR.

15. The method of claim 11, wherein the method comprises making RNA copies of HIV-1 cDNA with T7 polymerase.

16. The method of claim 11, wherein the method comprises detecting the presence or absence of HIV-1-specific nucleic acid in the amplified sample with a fluorescent label.

17. The method of claim 11, wherein the HIV-1-infected patient has been treated with an anti-HIV inhibitor within 1 month prior to or after being treated with at least one dose of glatiramer acetate.

18. The method of claim 11, wherein cells in the blood sample are removed to generate a plasma sample and RNA is prepared from the plasma sample.

19. The method of claim 18, wherein the plasma sample is subjected to ultracentrifugation prior to preparing RNA.

20. The method of claim 11, wherein, the cDNA is prepared using an HIV-1-specific primer and a reverse transcriptase.

* * * * *